United States Patent [19]

Ruminski

[11] Patent Number: 5,623,084
[45] Date of Patent: Apr. 22, 1997

[54] FLUOROALKENYL COMPOUNDS AND THEIR USE AS PEST REPELLENTS

[75] Inventor: Peter G. Ruminski, Ballwin, Mo.

[73] Assignee: Monsanto Company, St. Louis, Mo.

[21] Appl. No.: 443,645

[22] Filed: May 18, 1995

Related U.S. Application Data

[60] Continuation of Ser. No. 401,635, Mar. 8, 1995, Pat. No. 5,561,162, which is a division of Ser. No. 321,952, Oct. 12, 1994, Pat. No. 5,457,134, which is a division of Ser. No. 138,937, Oct. 18, 1993, Pat. No. 5,389,680, which is a continuation of Ser. No. 827,231, Feb. 3, 1992, abandoned, which is a continuation-in-part of Ser. No. 663,218, Mar. 1, 1991, abandoned.

[51] Int. Cl.$^6$ ................................................. C07C 309/67
[52] U.S. Cl. ................................................................ 558/54
[58] Field of Search .................................................. 558/54

[56] References Cited

U.S. PATENT DOCUMENTS

| | | | |
|---|---|---|---|
| 2,894,971 | 7/1959 | O'Rear et al. | 260/456 |
| 3,272,695 | 9/1966 | Frohberger et al. | 167/30 |
| 3,654,333 | 4/1972 | Brokke et al. | 260/453 R |
| 3,689,662 | 9/1972 | Brokke et al. | 424/301 |
| 3,780,050 | 12/1973 | Brokke | 260/306 |
| 4,362,672 | 12/1982 | Yamabe et al. | 260/544 F |
| 4,876,285 | 10/1989 | Peake | 514/746 |
| 4,950,666 | 8/1990 | Peake et al. | 514/227.5 |
| 4,952,580 | 8/1990 | Martinez et al. | 514/236.2 |
| 5,358,957 | 10/1994 | Maienfisch et al. | 514/342 |

FOREIGN PATENT DOCUMENTS

| | | |
|---|---|---|
| 0414600A1 | 8/1990 | European Pat. Off. . |
| 0432361 | 6/1991 | European Pat. Off. . |
| 49-17858 | 12/1970 | Japan . |
| 0024445 | 4/1974 | Japan . |
| 56-62825 | 5/1981 | Japan . |
| 63-172440 | 7/1988 | Japan . |

OTHER PUBLICATIONS

Kawada et al, Development of a New Fungicide, Mepronil, Journal of Pesticide Science vol. 10, 1985, 315–324.

*Primary Examiner*—Brian M. Burn
*Attorney, Agent, or Firm*—Grace L. Bonner; Arnold, White & Durkee

[57] ABSTRACT

Fluorinated alkene compounds useful for and methods of controlling nematodes, insects, and acarids that prey on agricultural crops. Polar compounds, for example, 3,4,4-trifluoro-3-butene-1-amine or 3,4,4-trifluoro-3-butenoic acid, are particularly useful for systemic control of pests. Novel method and intermediates for the preparation of 3,4,4-trifluoro-3-butene-1-amine are also provided.

2 Claims, No Drawings

FLUOROALKENYL COMPOUNDS AND THEIR USE AS PEST REPELLENTS

This application is a continuation of U.S. Ser. No. 08/401,635 filed on Mar. 8, 1995 (now U.S. Pat. No. 5,561,162) which is a divisonal of U.S. Ser. No. 08/321,952 filed Oct. 12, 1994, now U.S. Pat. No. 5,457,134, which is a divisional of U.S. Ser. No. 08/138,937 filed Oct. 18, 1993, now issued as U.S. Pat. No. 5,389,680, which is a continuation of U.S. Ser. No. 07/827,231 filed Feb. 3, 1992, now abandoned, which is a continuation-in-part of 07/663,218, filed March 1, 1991, now abandoned.

FIELD OF THE INVENTION

The present invention relates to certain fluoroalkenyl compounds, including, mono, di, and trifluoroalkenylamines, trifluoroalkenylcarboxylic acids, their derivatives and salts, and formulated compositions thereof. It also related to methods of controlling pests that prey on agricultural crops, such as nematodes, insects, and acarids. A novel method of preparing a trifluoroalkenylamine and novel intermediates for this method are also provided.

BACKGROUND OF THE INVENTION

Fluorinated alkenes have long been known to control nematodes and insects when applied to the soil. U.S. Pat. Nos. 3,510,503, 3,654,333, and 3,780,050 all disclose such compounds. More recently, U.S. Pat. No. 4,952,580 disclosed polyhaloalkenes useful as nematocides, some of which were said to have some downward systemic activity, that is, would control to some extent nematode infestation of the root system after application to the plant foliage. The majority of the compounds disclosed by these patents are nonpolar, which is a desirable characteristic for soil-applied pesticides, providing longer effective periods, but is much less effective for foliar application to achieve systemic effects. U.S. Pat. No. 4,950,666 discloses some polar difluoroalkenylalkane compounds useful as systemic insecticides and nematocides. However, there remains a need in the art for nematode, insect, and acarid control agents having improved systemic mobility, and desirably with low effective levels of use.

SUMMARY OF THE INVENTION

The present invention provides compounds, useful for controlling nematode, insect, and acarid infestation of a plant, having the structure

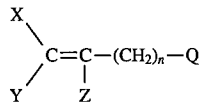

wherein n=1, 3, 5, 7, 9, or 11;

Q is $CH_2NHR_6$, $CH_2NO_2$, $CH_2N=CHR_2$, $CH_2N=C=O$, $CH_2N^+R_3R_4R_5W^-$, or $(C=O)-R_{11}$;

X, Y, and Z are independently H or F, provided that at least one of X and Y is F, and further provided that when Q is $(C=O)-R_{11}$ each of X, Y, and Z is F;

$W^-$ is an agronomically acceptable anion;

$R_2$ is an aromatic group;

each of $R_3$, $R_4$, and $R_5$ is independently hydrogen; a lower alkyl group, optionally substituted with at least one group selected from hydroxy, alkoxy, halo, nitro, amino, thiol, alkylthio, carboxyl, alkoxy-carbonyl, and phenyl; one of $R_3$, $R_4$, and $R_5$ is hydroxy and the other two are hydrogen; or $R_3$, $R_4$, and $R_5$ taken together with the nitrogen of Q form a cyclic quaternary ammonium group;

$R_6$ is hydrogen; an aliphatic group, optionally substituted with at least one group selected from hydroxy, alkoxy, halo, nitro, amino, thiol, alkylthio, carboxyl, alkoxycarbonyl, and phenyl; an amino acid amide of Q; $(C=O)-R_7$; $C_1-C_{12}$ aliphatic amines, optionally substituted with at least one group selected from hydroxy, alkoxy, halo, nitro, amino, thiol, alkylthio, carboxyl, alkoxycarbonyl, and phenyl; $C_2-C_{12}$ aliphatic carboxylic acids, their esters, thiol esters, and amides, all optionally substituted with at least one group selected from hydroxy, alkoxy, halo, nitro, amino, thiol, alkylthio, carboxyl, alkoxycarbonyl, and phenyl; dihydro-3-oxo-pyrazolidinyl; or phenyl or thiophene, optionally substituted with at least one group selected from hydroxy, alkoxy, halo, nitro, amino, thiol, alkylthio, carboxyl, alkoxycarbonyl, and phenyl;

or $R_6$ taken with the nitrogen of Q is guanidine; hydrazine; alkyl or aryl hydrazine, optionally substituted with at least one group selected from hydroxy, alkoxy, halo, nitro, amino, thiol, alkylthio, carboxyl, alkoxycarbonyl, and phenyl; or an alkyl or aryl sulfonamide, optionally substituted with at least one group selected from hydroxy, alkoxy, halo, nitro, amino, thiol, alkylthio, carboxyl, alkoxycarbonyl, and phenyl;

$R_7$ is $(C=O)-R_{14}$; $C_1-C_{12}$ aliphatic group optionally substituted with at least one group selected from hydroxy, alkoxy, halo, nitro, amino, thiol, alkylthio, carboxyl, alkoxycarbonyl, and phenyl; $C_2-C_{12}$ aliphatic carboxylic acid, esters, thiol esters, or amides thereof, all optionally substituted with at least one group selected from hydroxy, alkoxy, halo, nitro, amino, thiol, alkylthio, carboxyl, alkoxycarbonyl, and phenyl; or a N, O, or S group such that when taken with the carboxamide is a urea, semicarbizide, carbamate, or thiocarbamate group, all optionally substituted with an alkyl or aryl group, optionally substituted with at least one group selected from hydroxy, alkoxy, halo, nitro, amino, thiol, alkylthio, carboxyl, alkoxy-carbonyl, and phenyl;

$R_{11}$ is $-OR_{12}$, $-SR_{12}$, halogen, $-NHOH$, or $-NR_{12}R_{13}$; each of $R_{12}$ and $R_{13}$ is independently hydrogen; an aliphatic or an aromatic group, optionally substituted with at least one group selected from hydroxy, alkoxy, halo, nitro, amino, thiol, alkylthio, carboxyl, alkoxycarbonyl, and phenyl; a $C_1-C_{12}$ aliphatic amine, optionally substituted with at least one group selected from hydroxy, alkoxy, halo, nitro, amino, thiol, alkylthio, carboxyl, alkoxycarbonyl, and phenyl; a $C_2-C_{12}$ aliphatic carboxylic acid, esters, amides and salts thereof, optionally substituted with at least one group selected from hydroxy, alkoxy, halo, nitro, amino, thiol, alkylthio, carboxyl, alkoxycarbonyl, and phenyl;

or $R_{12}$ and $R_{13}$ taken together with the N of $R_{11}$ are a protein amino acid or a cyclic group selected from morpholine, piperidine, piperazine, or pyrrolidine, optionally substituted with at least one group selected from hydroxy, alkoxy, halo, nitro, amino, thiol, alkylthio, carboxyl, alkoxycarbonyl, and phenyl;

$R_{14}$ is OH, alkoxy, $NH_2$, or $NHNH_2$;

or any agronomically acceptable salt thereof;

provided that when n is 1 and each of X, Y, and Z is F, Q is not $CH_2NH_2$ or a mineral acid salt of $CH_2NH_2$.

Those skilled in the art will recognize that alternate substituents may be identified that will provide substantially equivalent results.

The present invention also provides methods of controlling nematode, insect, and acarid infestation of a plant by applying a compound as described above or, when systemic activity is desired, a compound of the following formula may be chosen:

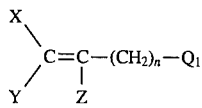

wherein n=1, 3, 5, 7, 9, or 11; $Q_1$ is $CH_2NHR$ or (C=O)—R; each of X, Y, and Z is independently H or F and at least one of X and Y is F, provided that when $Q_1$ is (C=O)—R each of X, Y, and Z is F; R is a group that has or is transformed after application to have polarity providing phloem mobility without reducing nematode-controlling controlling effectiveness; or any agronomically acceptable salt thereof. Preferred compounds for use in these methods are agronomically acceptable salts of 3,4,4-trifluoro-3-butene-1-amine, 3,4,4-trifluoro-3-butenoic acid, and its agronomically acceptable salts.

A method of preparing 3,4,4-trifluoro-3-butene-1-amine and novel intermediates, 3,4,4-trifluoro-3-butene-1-tosylate and 3,4,4-trifluoro-3-butene-1-mesylate, are also included in the present invention.

DETAILED DESCRIPTION OF THE INVENTION

The novel compounds of the present invention are useful for controlling nematode, insect, and acarid infestation of a plant. Many of these compounds, being polar, are highly effective for systemic control, that is, when applied to the foliage or stems of a plant they are able to move through the phloem and xylem of the plant and provide control of nematodes, insects, or acarids at other locations on the plant. It is believed that this control mechanism is a repelling or antifeedant action, rather than a harming action. Others, particularly the nonpolar compounds are effective only when applied directly to the soil. Some compounds can provide both types of control.

The present methods for systemic control of nematodes, insects, and acarids use the phloem mobile compounds of the present invention or those compounds having a mono-, di-, or trifluoroalkene group bearing a $CH_2NHR$ substituent or a trifluoroalkene group bearing a (C=O)—R substituent, having sufficient polarity to allow for phloem-mobility without eliminating the nematode-controlling activity of the fluoroalkene moiety. There are several different theories concerning phloem mobility, such as what polarity characteristics compounds must have to be sufficiently phloem mobile in order to be relocated downward in a plant. It has been proposed that the polarity of the molecule as a whole must be sufficient for the molecule to be retained in the phloem, but not be so polar as to not enter at all.

To effectively control nematodes or other pests systemically by application to the above-ground surfaces of a plant, compounds must be capable of passing through the cuticle of the foliage or stem of a plant, passing into the phloem, and remaining there long enough to be transported throughout the plant so as to move to untreated areas including the roots. There they may leak out or in some way contact the pests to such an extent that they are killed or repelled and the damage they would do to the plant is reduced or eliminated. During these steps of transport from the treated areas of leaves or stems throughout the plant, a compound may undergo chemical reactions, such as hydrolysis, or biological reactions, such as enzymatic actions. In addition, compounds may be devised which, when placed on the plant, prior to absorption into the plant, may undergo reactions that result in a compound that is readily absorbable, translocatable, and effective in preventing pest damage. An example of such compounds are those having UV-labile protecting groups which when exposed to natural light undergo reaction and result in active and mobile compounds. Another example is silylated amine derivatives.

Therefore, what is placed on the foliage or stem of the plant may not be the compound that is actually transported or the compound that actually controls the pests. Thus, the methods of the present invention provide for compounds that may be transformed through chemical or biological reactions to have proper polarity for systemic activity.

The methods of the present invention include applying 3,4,4-trifluoro-3-butene-1-amine or its salts to the plant locus, preferably to the foliage. Also included are compositions comprising an aqueous solution of 3,4,4-trifluoro-3-butene-1-amine or its salts in an agronomically acceptable carrier.

In the methods described above, in order to control nematodes it is preferred that n is 1 and X, Y, and Z are all F, and more preferably $Q_1$ is then $CH_2NH_3^+W^-$, that is, a salt of 3,4,4-trifluoro-3-butene-1-amine. When $Q_1$ is $CH_2NHR_6$, $R_6$ is preferably an alpha-amino acid linked by a peptide (amide) bond, more preferably a protein amino acid. When $Q_1$ is (C=O)—$R_{11}$, $R_{11}$ is preferably hydroxyl and the compound is thus 3,4,4-trifluoro-3-butenoic acid or a salt thereof, including a salt formed with 3,4,4-trifluoro-3-butene-1-amine, that is, 3,4,4-trifluoro-3-butene-1-amine 3,4,4-trifluoro-3-butenoate.

$W^-$ may be any agronomically acceptable anion. This includes, but is not limited to chloride, iodide, bromide, oxalate, sulfate, phosphate, citrate, acetate, or a fluoroalkene carboxylate, for example, $F_2C=CFCH_2COO^-$.

In addition to the compounds specifically described above, all agronomically acceptable salts of the compounds are within the scope of the present invention. For example, a compound of the present invention having a free amine group may also exist as the protonated form having various anions associated therewith, for example, but not limited to, chloride, bromide, iodide, phosphate, oxalate, sulfate, citrate, and acetate. In addition, a fluoroalkene carboxylate ion, such as $F_2C=CFCH_2COO^-$, may be the counter-ion. A compound of the present invention having a carboxylic acid or hydroxyl group may exist as the salt having various cations associated therewith, for example, but not limited to, alkali earth metals, such as sodium, calcium, and potassium; magnesium; or quaternary ammonium ions, such as ammonium, mono-, di-, or trialkylammonium, for example, isopropylammonium, or pyridinium. In addition, a fluoroalkenyl ammonium ion, such as $F_2C=CFCH_2CH_2NH_3^+$, may be the cation. All such compounds and others having similar characteristics, being agronomically acceptable, are encompassed by the present invention.

As used herein, the term "halo" "halide" or "halogen" means fluorine, chlorine, iodine, or bromine or cognates thereof.

The term "alkyl" means straight-chain or branched groups of from one to about seven carbon atoms. The term "lower alkyl" means a such a group containing from one to about four carbon atoms. The term "aliphatic" means saturated or unsaturated, branched or straight-chain, alkyl groups having from one to ten carbon atoms.

The term "alkoxy" means a lower alkyl group bonded via an oxygen atom. The term "alkylthio" means a lower alkyl group bonded via a sulfur atom. The term "alkoxycarbonyl" means the lower alkyl ester of a carboxyl group.

The term "aliphatic amine" means an aliphatic group wherein at least one hydrogen is replaced with —$NH_2$. The term "aliphatic carboxylic acid, its esters, thiol esters, and amides" means an aliphatic group wherein at least one carbon is a carboxylic group, —COOH, or is the lower alkyl ester, lower alkyl thiol ester, or amide thereof.

The term "aromatic group" or "aryl" means phenyl, optionally substituted with at least one group selected from hydroxy, alkoxy, halo, nitro, amino, thiol, alkylthio, carboxyl, alkoxycarbonyl, and phenyl. It should be obvious to one of ordinary skill in the art that heterocycles could also be used for the aromatic group, for example, thiadiazole, pyridine, thiazole, isothiazole, oxazole, pyrazole, triazole, benzothiazole, thiophene, furan, and the like, all of which may also be optionally substituted.

As used herein, the phrase "amino acid amide of Q" (or $Q_1$) means that $R_6$ is an amino acid coupled via a peptide (amide) bond to the N of $CH_2NHR_6$. This amino acid may be a natural, i.e., protein, amino acid or a nonnaturally occurring amino acid. The amino group of the amino acid may be a substituent of any carbon in the group, for example, alpha, beta, or gamma to the carbonyl.

The term "alkyl or aryl hydrazine" means a hydrazine group substituted with a lower alkyl or phenyl group, which in turn may be optionally substituted. The term "alkyl or aryl sulfonamide" means a sulfonamide group substituted with a lower alkyl or phenyl group, which in turn may be optionally substituted.

COMPOUND SYNTHESIS

The compounds of the formula above wherein X, Y, and Z are F and Q is a —$CH_2N$— derivative are generally prepared by first obtaining the desired trifluoroalkenylamine, which when n equals 1 is 3,4,4-trifluoro-3-butene-1-amine. One method of preparing this compound is disclosed in Example 6 of U.S. Pat. No. 4,952,580, the full text of which is incorporated herein by reference. The present invention provides an improved and novel method of making this compound. Surprisingly, 4-bromo-1,1,2-trifluoro-1-butene, which is commercially available, may be directly converted by first reacting it with a tosylate salt, for example, silver tosylate, a mesylate salt, or other sulfonic acid leaving group. The resulting intermediate, for example, 3,4,4-trifluoro-3-butene-1-tosylate or 3,4,4-trifluoro-3-butene-1-mesylate, is a novel compound. This step is followed by conversion to the phthalimide derivative using a phthalimide salt, such as potassium. Advantageously, this may be accomplished without first isolating the tosylate or mesylate intermediate. The phthalimide is then converted to the desired amine by reaction with hydrazine. This novel process for preparing 3,4,4-trifluoro-3-butene-1-amine has the advantage of having an improved yield compared to the prior reported synthesis method, which is at least partially attributable to avoiding the elimination of hydrogen bromide during the conversion of the bromo compound. N-(3,4,4-trifluoro-3-butenyl)phthalimide is thus produced in greater than 80 percent yield and converted to the desired amine in greater than 85 percent yield. Also, advantageously, when silver tosylate is the reactant chosen to provide the leaving group, the silver ions may be recovered and silver tosylate regenerated.

Longer chain alkenyl amines may be made through several routes. For example, to produce a compound of the present invention wherein n equals 3, ethylene oxide can be reacted with 4-bromo-1,1,2-trifluoro-1-butene by known methods to produce 6-hydroxy-1,1,2-trifluoro-1-hexene. This compound may then be converted to the amine salt using tosyl chloride and phthalimide as described above for the butene. Alternatively, 1,1,2-trichloro-1,2,2-trifluoroethane (F113) may be reacted with a terminal alkene or alkyne bromo compound under redox conditions, as described in *Tetrahedron Letters*, 31, pp 1307–1308, 1990. The reaction product is subsequently dechlorinated with Zn to produce a trifluoroalkene bromide, which can be converted to the desired amine as described above for the butene. A third method is exemplified in Synthesis Example 40, below.

Difluoro alkenyl amines may be made by two different methods, depending on the position of the fluorines. To produce a terminal difluoro compound, such as 4,4-difluoro-3-butene-1-amine hydrochloride, the following route may be used:

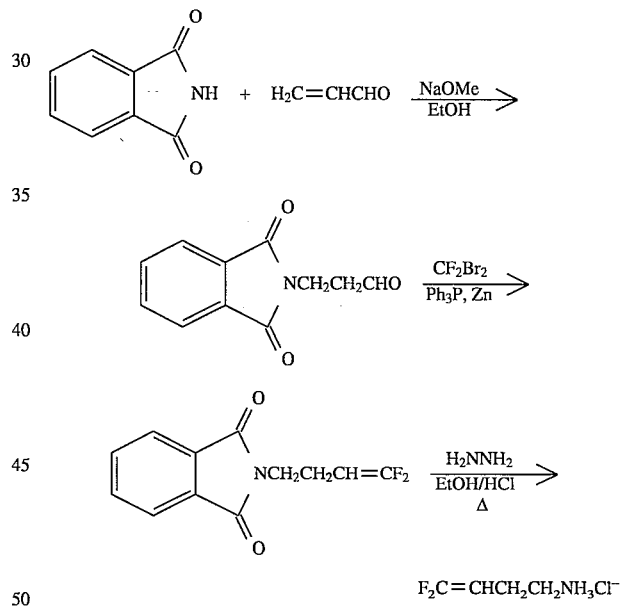

The other difluoro compounds, that is, wherein one of X and Y is H and Z is F, are made by the following route:

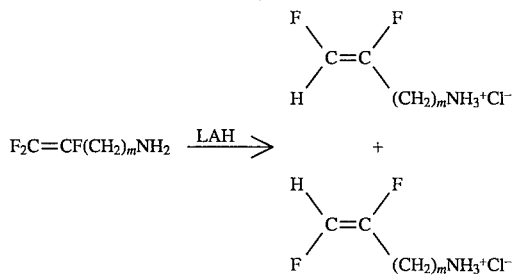

wherein m is 2, 4, 6, 8, 10, or 12, LAH is lithium aluminum hydride. The E and Z forms may be isolated by distillation from the mixture of products obtained from this reduction.

Likewise, monofluoro compounds of the present invention are made by two different routes depending on whether the fluorine is terminal or internal, as illustrated in the following schematics:

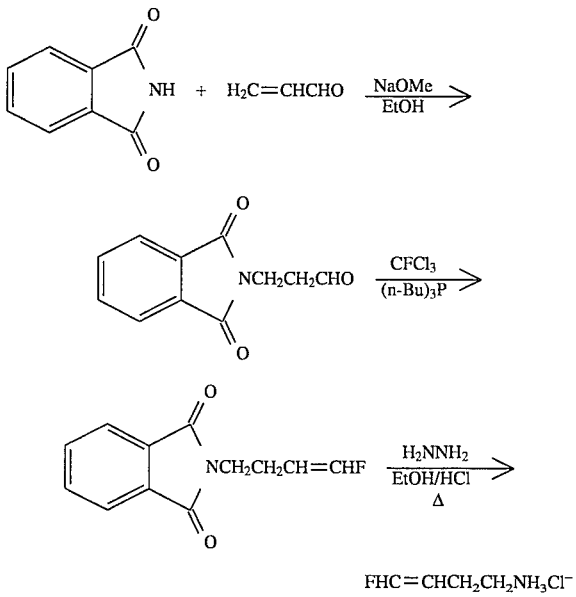

To produce an internal monofluoro compound, the following scheme may be used:

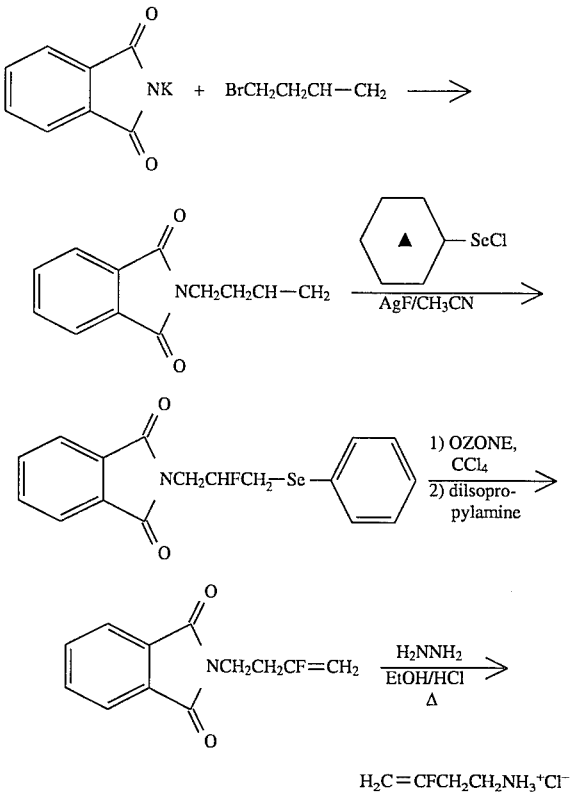

Many of the other compounds of the present invention where Q is $CH_2NHR_6$ are then easily prepared by reacting a selected reactant with the appropriate fluoroalkenyl amine or a salt thereof by methods generally known to those skilled in the art. For example, to prepare amide derivatives, wherein $R_6$ is a —(C=O)-derivative, the appropriate acid is reacted with the selected fluorinated alkenylamine by conventional techniques. The acid may be in the form of the acid halide or anhydride for the most efficient reaction with the amine. For example, when $R_6$ is (C=O)—$CF_3$, trifluoroacetic anhydride is used. When the succinamic acid derivative is desired, succinic anhydride may be used, and when the oxalic acid derivative is desired, the acid chloride may be used.

Where $R_6$ is an alpha-amino acid linked by a peptide (amide) bond to the nitrogen of $CH_2NHR$, that is, when $R_6$ taken with the nitrogen is an alpha-amino acid amide, typical peptide or amide coupling reagents, such as carbonyldiimidazole or DCC, may be used to effect the peptide (amide) bond. For substituted acid groups, any functional group which could affect or be affected by the peptide (amide) bonding must be properly protected. For example, an amine functionality would be protected by a t-BOC group. Acids or alcohols can be protected as benzyl or t-butyl esters or ethers, respectively. Thiols can be protected by a trityl group. Deprotection, to produce the desired compound, would follow, using known methods.

Where $R_6$ is an aliphatic carboxylic acid, there are two synthetic routes. The desired fluoroalkenylamine may be reacted with the appropriate electrophilic reagent, for example, a haloalkylcarboxylate ester. The resulting ester may be used or hydrolyzed to the free acid, which may then be derivatized by known methods to its salts, amides, and thiol esters. Alternatively, the bromofluoroalkene may be reacted with the appropriate amino acid.

Where $R_6$ is a lower aliphatic group, the selected fluoroalkenylamine is reacted with the appropriate electrophilic agent, for example, an alkyl halide, such as methyl iodide. The amine is preferably present in excess to the alkyl halide in order to minimize further amine substitution.

Where $R_6$ is a $C_1$-$C_{12}$ alkyl amine, the bromide or tosylate, instead of the amine, is generally used as the starting material and reacted with excess of the desired alkyldiamine, having one amine group protected. Thereafter, deprotection by known methods will result in the desired product.

Where $R_6$, taken with the nitrogen of the Q or $Q_1$ group $CH_2NHR_6$, is guanidine, the selected fluoroalkenylamine, in the form of a salt as described above, is reacted with cyanamide.

Where $R_6$ taken with the nitrogen of the Q or $Q_1$ group $CH_2NHR_6$ is an alkyl or aryl sulfonamide, optionally substituted, the selected fluoroalkenylamine is reacted with the appropriate sulfonyl chloride, for example, tosyl chloride.

Where $R_6$ taken with the nitrogen of the Q or $Q_1$ group $CH_2NHR_6$ is a urea, carbamate, thiocarbamate, semicarbizide, or hydrazine, the selected fluoroalkenylamine is first converted to the isocyanate, i.e., where Q is $CH_2N=C=O$. This isocyanate is prepared by reacting the amine with diphenylcarbamoyl chloride, followed by high temperatures to produce the isocyanate as in the following schematic.

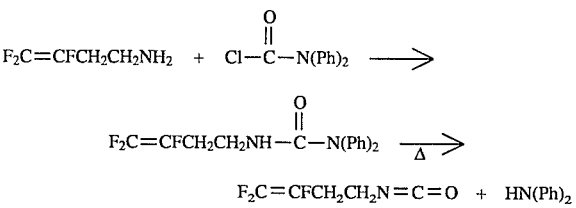

From the isocyanate the other compounds may be made by reaction with ammonia or amines to produce ureas; alcohols to produce carbamates; thiols to produce thiocarbamates; or hydrazines to produce semicarbizides. In the last instance, the hydrazine must be protected, for example, with a t-BOC group and subsequently deprotected to produce the semicarbizide.

Compounds wherein Q is $CH_2N=CH-R_2$ are also prepared from the appropriate fluoroalkenylamine, for example, 3,4,4-trifluoro-3-butene-1-amine. It is reacted using known methods with the appropriate aromatic aldehyde, preferably a benzaldehyde, for example, p-(N,N-dimethylamino)-benzaldehyde or 2-hydroxy-5-nitrobenzaldehyde.

Compounds wherein Q is $CH_2N^+R_3R_4R_5W^-$ may sometimes be prepared from the fluoroalkenylamine, for example, 3,4,4-trifluoro-3-butene-1-amine. The amine group is quaternized by known methods, for example by an excess of alkyl halide, for example methyl iodide. Thus the compound 3,4,4-trifluoro-3-butenyl trimethyl ammonium iodide could be produced.

For other compounds wherein Q is $CH_2N^+R_3R_4R_5W^-$, the fluoroalkenyl bromide may be used. For example, when $R_3$, $R_4$, and $R_5$ are taken together with the nitrogen to form a cyclic quaternary ammonium group, the appropriate cyclic amine, for example hexamethylenetetramine, is reacted with the fluoroalkenyl bromide to produce the desired quaternary ammonium compound. When one of $R_3$, $R_4$, and $R_5$ is a hydroxyl group, the compound is prepared by reacting the fluoroalkenyl bromide with excess O-trimethylsilylhydroxylamine to produce the O-trimethylsilyl-protected fluoroalkenylhydroxylamine, which is then hydrolyzed with methanol, followed by treatment with acid, to produce the desired hydroxyl amine salt.

The compound wherein Q is $CH_2NO_2$ may be prepared by known methods from the fluoroalkenyl bromide and silver nitrite.

The compounds of the present invention that are trifluoroalkenecarboxylic acids and derivatives, that is, where Q is $(C=O)-R_{11}$ (and X, Y, and Z are F) are similar to some of the compounds disclosed in U.S. Pat. No. 4,950,666, but cannot be made by the same Wittig reaction procedure. They are prepared by a completely different route, by converting 4-bromo-1,1,2-trifluoro-1-butene to the alcohol via an ester intermediate. For example, phenyl acetic acid is used to produce the phenyl acetate ester of trifluorobutene, then hydrolyzed to produce trifluorobutenol, and then oxidized to the acid, as in the following schematic:

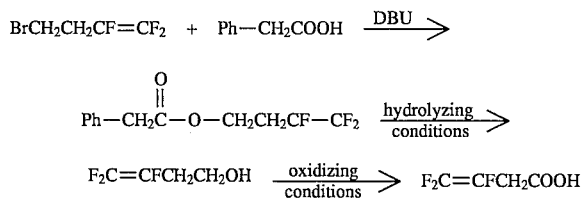

Longer chain acids, where n is 3, 5, etc., may be made in the same manner from the longer chain halides made as described above. Derivatives of these acids, e.g., salts, ester, amides, etc., may be readily made by methods known to those skilled in the art.

Details of such reactions are given in the following specific Synthesis Examples, which are provided for illustration and are not meant to be limiting in any way.

SYNTHESIS EXAMPLE 1

Preparation of 3,4,4-trifluoro-3-butene-1-amine and its salts.

(a) To 25 g (0.0896 mole) silver tosylate in 100 mL acetonitrile is slowly added 13.2 g (0.07 mole) 4-bromo-1,1,2-trifluoro-1-butene with stirring, at room temperature. The reaction mixture, protected from the light, is then heated and stirred overnight at reflux. After cooling, the precipitate is filtered off, and the solvent removed from the filtrate under vacuum. Ethyl acetate, 100 mL, is added to the residue of the filtrate and then washed three times with water and dried over magnesium sulfate. To this ethyl acetate solution of 3,4,4-trifluoro-3-butene tosylate is added 25 mL DMF and 16.7 g (0.09 mole) potassium phthalimide. This reaction mixture is stirred at reflux for 24 hrs. After cooling, the precipitate is filtered off and washed with ethyl acetate, which is combined with the filtrate, washed once with water, once with 5% NaOH solution, and then three times with water, and lastly, dried over magnesium sulfate. The solvent is removed under vacuum to yield 14.45 g N-(3,4,4-trifluoro 3-butenyl)phthalimide as a tan solid.

(b) To 13.91 g (0.054 mole) of the product of step a, dissolved in 100 mL of ethanol, is added 1.76 g (0.054 mole) anhydrous hydrazine. The reaction mixture is then stirred at reflux for 3 hrs. Conc. HCl, 40 mL, is then added slowly through the reflux condenser, and the mixture stirred two more hrs at reflux. After cooling, the reaction mixture is diluted with water; the precipitate is filtered off and washed with additional water, which is combined with the filtrate. The combined filtrates are washed with ether and the ether layer discarded. The aqueous layer is cooled in an ice bath and then 50% NaOH added until the solution is basic. The aqueous layer is then extracted twice with chloroform and the combined chloroform extractions, containing the desired amine are dried over magnesium sulfate.

(c) To isolate the hydrochloride salt of the desired amine, excess HCl gas is bubbled into the chloroform solution of step b. After stirring for 15 mins., the chloroform is removed under vacuum to yield 7.4 g of 3,4,4-trifluoro-3-butene-1-amine hydrochloride as a white solid. m.p. 191°–193° C. This is Compound 1 used in the biological tests described below.

(d) Other salts of the amine may be prepared in a like manner or from the hydrochloride salt by methods generally known in the art. For example, the hydrochloride salt may be neutralized back to the free amine. Excess free amine is then added to the various acids dissolved in methanol to form the desired salts.

SYNTHESIS EXAMPLE 2

Preparation of N-(3,4,4-trifluoro-3-butenyl)glycine hydrochloride (Compound 9)

(a) 34.4 g (0.34 mole) triethylamine is added to a slurry of 55 g (0.34 mole) of Compound 1, prepared as above, in 600 mL tetrahydrofuran (THF). 16.1 g (0.105 mole) of methylbromoacetate is then added dropwise at room temperature and the reaction mixture is stirred at room temp. for 4 hrs. The precipitate is filtered off and the solvent from the filtrate removed under vacuum. Ether is added to the residue and this is stirred for 20 min. Additional precipitate is filtered off, and excess anhydrous HCl gas is bubbled into the ether filtrate. The resulting precipitate is filtered, washed with ether and dried under vacuum to yield 23.4 g of the methyl ester of N-(3,4,4-trifluoro-3-butenyl)glycine hydrochloride, Compound 8, as a white solid, a 96% yield.

(b) 19 g (0.081 mole) of Compound 8 is refluxed overnight in 90 mL of 6N HCl, After removal of the solvent under vacuum, the residue is stirred for 2 hrs in ether. The precipitate is filtered, washed with ether and dried under vacuum to yield 16.25 g of the title compound, as a white solid, a 92% yield. m.p.: 186°–8° C.

SYNTHESIS EXAMPLE 3

Preparation of N-(3,4,4-trifluoro-3-butenyl)valine hydrochloride (Compound 10)

(a) 7.39 mL (0.053 mole) triethylamine is added to a solution of 8.88 g (0.053 mole) DL-valine methyl ester hydrochloride in 75 mL DMF under nitrogen. 4 g (0.021 mole) 4-bromo-1,1,2-trifluoro-1-butene is added dropwise to the resulting slurry and the reaction stirred for 7 days. The solvent is removed under vacuum. Ether is added to the residue and the precipitate filtered off. The ether from the filtrate is removed under vacuum. The residue is chromatographed by HPLC (7% ethyl acetate/hexane) and 0.33 g of desired amine isolated, taken up in ether and treated with excess HCl gas. The resulting precipitate is filtered and dried to yield 0.29 g of the methyl ester of N-(3,4,4-trifluoro-3-butenyl)valine hydrochloride, Compound 49.

(b) 0.47 g (0.0017 mole) of Compound 49 is refluxed overnight in 10 mL of 6N HCl. The reaction mixture is cooled and the solvent removed under vacuum. The residue is slurried in ether and the product filtered off to yield 0.43 g of the title compound, as a white solid, a 98% yield.

SYNTHESIS EXAMPLE 4

Synthesis of N,N'-bis(3,4,4-trifluoro-3butenyl)ethanediamide (Compound 21)

0.79 g (0.0062 mole) oxalyl chloride is added slowly to 4 g (0.0248 mole) of Compound 1 and 3.72 g (0.037 mole) triethylamine in 30 mL THF. This is stirred overnight at room temp. The precipitate is filtered off and the solvent from the filtrate removed under vacuum. The residue is slurried in water for 1 hr. The precipitate is filtered, washed with water and dried. The crude product is recrystallized from ethyl acetate to yield 0.46 g of the title compound, as a tan solid, a 24% yield. m.p. 139°–141° C.

SYNTHESIS EXAMPLE 5

Synthesis of 4-oxo-4-[(3,4,4-trifluoro-3butenyl)amino]butenoic acid (Compound 22)

0.8 g (0.005 mole) of Compound 1 is mixed with (0.005 mole) succinic anhydride in 30 mL THF. To this mixture is added 0.015 mole triethylamine with stirring. The mixture is stirred at room temperature for 48 hrs. The solvent is evaporated off, and the residue is taken up in water and acidified with conc. HCl. The desired product is filtered out and recrystallized from a mixture of ethyl acetate and cyclohexane to yield 0.7 g of the title compound, as needle-like crystals. m.p. 64°–66° C.

SYNTHESIS EXAMPLE 6

Synthesis of 4-nitro-2-[[(3,4,4-trifluoro-3butenyl)imino]methyl]-phenol (Compound 23)

To 0.005 mole 5-nitrosalicylaldehyde in 20 mL ethanol is added 0.005 mole NaOH as 10% aqueous solution. To this is added 0.005 mole of Compound 1 in 20 mL ethanol. This is stirred for 3 hrs at room temp. and then at 50° C for 5 hrs. A little water is added while the reaction mixture is hot. On cooling, crystals form to yield 0.6 g of the title compound, as yellow needle-like crystals. m.p. 96°–8° C.

SYNTHESIS EXAMPLE 7

Synthesis of N-(3,4,4-trifluoro-3-butenyl)hexamethylene bromide (Compound 26)

10 g (0.053 mole) 4-bromo-1,1,2-trifluoro-1-butene, 3.7 g (0.026 mole) hexamethylenetetramine and 27 mL chloroform are heated at reflux for 6.5 hrs. The precipitate is filtered from the hot reaction mixture and washed with 50 mL hot chloroform. The product is dried under vacuum to yield 1.1 g of the title compound, as a while solid, a 13% yield.

SYNTHESIS EXAMPLE 8

Synthesis of 3,4,4-trifluoro-N-hydroxy-3-butene-1-amine hydrochloride (Compound 27)

7.5 g (0.027 mole) 3,4,4-trifluoro-3-butene tosylate is added to 15 g O-TMS hydroxyl amine in a flame-dried pressure tube, flushed with nitrogen. The tube is capped and the reaction mixture stirred overnight at 75° C. After decanting off the liquid from the precipitate, the liquid is distilled and the product which boils at 29° C. at 1 mmHg is collected and yields 0.8 g of O-TMS protected title compound. This is stirred overnight in 5 mL of methanol. Excess HCl gas is then bubbled into the reaction mixture. The solvent is removed under vacuum and the product dried to yield 0.6 g of the title compound, as a viscous yellow oil.

SYNTHESIS EXAMPLE 9

Synthesis of 2-(3,4,4-trifluoro-3-butenyl)hydrazide benzoic acid (Compound 28)

7 g (0.037 mole) 4-bromo-1,1,2-trifluoro-1-butene is added to 20 g (0.147 mole) benzoyl hydrazine and 3.7 g (0.037 mole) triethylamine in 60 mL DMF and the mixture is stirred for 2 days at room temp. The solids are filtered off and the solvent from the filtrate removed under vacuum. Ether is added to the residue and this is slurried for 1 hr. The precipitates are filtered off. Ether is removed from the filtrate under vacuum. The residue is chromatographed by HPLC (40% ethyl acetate/hexane) to yield 1.35 g of the title compound, as a light yellow solid, a 15% yield. m.p. 74°–6° C.

SYNTHESIS EXAMPLE 10

Synthesis of N-(3,4,4-trifluoro-3-butenyl)hydrazine hydrochloride (Compound 29)

1 g (0.0041 mole) of Compound 28, prepared as described in Example 9, is refluxed overnight in 10 mL of 6N HCl. After cooling, a precipitate by-product forms. The aqueous layer is washed four times with ether. The water is removed under vacuum to yield 0.6 g of the title compound, as a brown gooey solid, a 83% yield.

SYNTHESIS EXAMPLE 11

Synthesis of N-(3,4,4-trifluoro-3-butenyl)guanidine hydrochloride (Compound 30)

3 g (0.0186 mole) of Compound 1 and 0.78 g (0.0186 mole) cyanamide are refluxed in 25 mL of absolute ethanol for 4 days. The solvent is removed under vacuum and the residue dried under vacuum to yield 3.66 g of the title compound, as an amber viscous oil, a 97% yield.

SYNTHESIS EXAMPLE 12

Synthesis of 3,4,4-trifluoro-3-butenyl nitrate (Compound 31)

2.6 g (0.14 mole) 4-bromo-1,1,2-trifluoro-1-butene is added dropwise to 4 g (0.026 mole) silver nitrate in 30 mL CH₃CN. This is stirred overnight in the dark at room temperature. The precipitate is filtered off and the solvent removed under vacuum. Water is added to the residue and the product extracted into ether. The ether is washed three times with water, dried over magnesium sulfate, and removed under vacuum to yield 250 mg of crude material which is distilled to give the title compound. b.p. 25°–28° C. at 0.85 torr.

SYNTHESIS EXAMPLE 13

Synthesis of N-(3,4,4-trifluoro-3-butenyl)urea (Compound 32)

1.5 g (0.0124 mole) TMS isocyanate is added to 2 g (0.0124 mole) of Compound 1 and 2.5 g (0.024 mole) triethylamine in 14 mL THF. The mixture is stirred overnight at room temp. and then for 2 hrs at 70° C. After cooling, the precipitate is filtered off and the solvent removed under vacuum. The resulting solid is slurried in ether. The ether is decanted from the insoluble material and removed under vacuum. Methanol is added to the residue, stirred overnight at room temperature, and then removed under vacuum. The residue is slurried in ether/pet. ether (1:1); the solid is filtered off and dried under vacuum to yield 0.6 g of the title compound, as a white solid, a 30% yield. m.p. 86°–88° C.

SYNTHESIS EXAMPLE 14

Synthesis of N-(p-trifluoromethylbenzenesulfonyl)-3,4,4-trifluoro-3-butene-1-amine (Compound 33)

Compound 1 (0.01 mole) is mixed with 100 mL methylene chloride and added to p-trifluoromethylbenzenesulfonyl chloride (0.01 mole) in 20 mL methylene chloride. The mixture is cooled and stirred, and 0.023 mole triethylamine is added. After stirring for 4 h at room temperature, 100 mL water is added and the two layers separated. The methylene chloride layer is washed with a $NaHCO_3$ solution in water and dried over magnesium sulfate. The solvent is evaporated, and the white residue recrystallized from ethyl acetate and cyclohexane to yield 2.6 g of the title compound as white crystals. m.p. 68°–70° C.

SYNTHESIS EXAMPLE 15

Synthesis of 2-amino-N-(3,4,4-trifluoro-2butenyl)propanamide hydrochloride (Compound 35)

(a) To 3.8 g (0.02 mole) N-t-BOC L-alanine in 40 mL anhydrous THF is added 3.2 g (0.02 mole) carbonyldiimidazole with gas evolution. After 1 hr., 3.6 g 3,4,4-trifluoro-3-butene-1-amine, prepared as in Example 1 above, is added and the reaction mixture stirred overnight at room temperature. The solvent is removed under vacuum. Water is added to the residue and the reaction product extracted into ether. The ether is washed three times with water, dried over magnesium sulfate, and removed under vacuum to yield 4.31 g of the t-BOC-protected analog of the title compound (Compound 34) as a white solid, a 73% yield. m.p. 78°–9° C.

(b) 1.5 g (0.0051 mole) of Compound 34 is dissolved in ether, and excess HCl gas is bubbled in. The reaction is stirred for 5 hrs at room temperature. The resulting white precipitate is filtered, washed with ether and dried under vacuum to yield 1.1 g of the title compound as a white solid, a 98% yield. m.p. 164°–6° C.

SYNTHESIS EXAMPLE 16

Synthesis of 3,4,4-trifluoro-3-butenoic acid (Compound 44) and its salts.

(a) 98 g (0.52 mole) 4-bromo-1,1,2-trifluoro-1-butene is added slowly to 50 g (0.37 mole) phenylacetic acid and 55.9 g (0.37 mole) 1,8-diazaobicyclo[5.4.0]undec-7-ene (DBU) in 400 mL $CH_3CN$. This is stirred at reflux for 2 days. After cooling, the solvent is removed under vacuum. Water is added to the residue and the product is extracted into ether. The ether is washed two times with 5% NaOH, two times with water, dried over magnesium sulfate, and removed under vacuum to yield 40.87 g phenylacetic acid trifluorobutenyl ester. This ester is added to 7.2 g (0.18 mole) of NaOH dissolved in 70 mL water. This is vigorously stirred overnight at room temperature. Ether is added to the reaction mixture to extract the product. The separated ether layer is dried over magnesium sulfate and distilled. The product is collected yielding 15.78 g 4-hydroxy-1,1,2-trifluoro-1-butene as a clear liquid. b.p. 120° C. at 760 mmHg.

(b) To 84.27 g (0.843 mole) chromium trioxide in 500 mL acetic acid and 75 mL water, is added dropwise 26.43 g (0.21 mole) of the alcohol produced in (a), keeping the temperature below 10° C. After addition is complete, the reaction mixture is stirred at 5° C. for 2 hrs then at room temperature. The mixture is then diluted with 1 liter water and extracted two times with ether. The combined ether layers are washed three times with water, dried over magnesium sulfate, and the solvent removed under vacuum. The residue is short path distilled at 1 mmHg and the fraction boiling at about 55° C. collected. This distillate is dissolved in ether and then extracted two times with saturated $NaHCO_3$. The combined $NaHCO_3$ layers are washed three times with ether and then acidified with conc. HCl. The product is then extracted into ether. The ether is washed three times with water, dried over magnesium sulfate, and removed under vacuum to yield 8.22 g of the title compound as a clear liquid.

(b) Compound 44 may be prepared and then neutralized to any agronomically acceptable salt by known methods. This includes the salt of a trifluorobutene amine, such as 3,4,4-trifluoro-3-butene-1-amine, prepared as in Example 1.

SYNTHESIS EXAMPLE 17

Synthesis of 3,4,4-trifluoro-3-butene-1-amide (Compound 45)

1.15 g (0.0071 mole) carbonyldiimidazole is added to 1 g (0.0071 mole) Compound 44, prepared as in Example 16, dissolved in 20 mL of anhydrous THF. After stirring for 20 minutes (min), excess anhydrous $NH_3$ gas is bubbled into the reaction mixture, and the mixture is stirred overnight at room temperature. The solvent is then removed under vacuum. Ethyl acetate is added to the residue and this is extracted two times with 10% HCl, dried over magnesium sulfate, and removed under vacuum. The crude product is then sublimed (50°–55° C. at 1 mmHg) to yield 0.39 g of the title compound as a white solid.

SYNTHESIS EXAMPLE 18

Synthesis of 2,2,2-Trifluoro-N-(3,4,4-trifluoro-3-butenyl)acetamide (Compound 50)

1.7 g (0.008 mole) trifluoroacetic anhydride is slowly added to 1.07 g (0.0066 mole) of Compound 1 and 0.67 g (0.0066 mole) triethylamine in 10 mL of THF and the mixture is stirred overnight at room temperature. The solids are filtered off and the solvent is removed under vacuum. Water is added to the residue and the product is extracted into ether. Triethylamine, 0.5 mL, is added to the ether and the ether is washed four times with water, dried over magnesium sulfate, and removed under vacuum. The product is distilled from the residue to yield 0.5 g of the title compound as a clear liquid, a 35% yield.

SYNTHESIS EXAMPLE 19

Synthesis of 1,1,2-trifluoro-4-isocyanato-1-butene (Compound 72)

(a) Anhydrous pyridine and 0.033 mole of Compound 1 are mixed and cooled to 0° C. 0.022 mole of diphenylcarbamyl chloride is added and the reaction mixture stirred overnight at room temperature under nitrogen. The resulting slurry is added to ice water and the precipitate filtered off and washed with water. The precipitate is dissolved in an ether/ethyl acetate solution, dried over magnesium sulfate, and concentrated. The resulting precipitate is recrystallized from hot ethyl acetate/hexane to yield 4.57 g N,N-diphenyl-N'-(3,4,4-trifluoro-3-butenyl)urea, a 65% yield. m.p. 116°–117° C.

(b) 0.016 mole of the urea of step (a) is heated under nitrogen until no vapors are no longer formed from the pyrolysis. The title compound is collected as it distills over to yield 1.67 g as a clear oil.

SYNTHESIS EXAMPLE 20

Synthesis of 4-methyl-N-[[(3,4,4-trifluoro-3-butenyl)amino]-carbonyl]benzenesulfonamide (Compound 75)

0.01 mole of Compound 1 in 40 mL THF is stirred at room temperature while adding 0.01 mole p-toluenesulfonylisocyanate. Cooling is effected and 0.01 mole triethylamine is added. The mixture is stirred at room temperature for 48 hrs. and the solvent removed under vacuum. The residue is taken up in methylene chloride and washed three times with 50 mL water. The solvent is dried with magnesium sulfate and evaporated. The residue is recrystallized from ethanol to yield 1.1 g of the title compound as white crystals. m.p. 134°–136 C.

SYNTHESIS EXAMPLE 21

Synthesis of 4-amino-1,1-difluoro-1-butene hydrochloride (Compound 46)

(a) 100 g (0.68 mole) phthalimide in 250 mL ethanol and 0.08 g sodium methoxide is heated to 48° C. and 50.8 g (0.91 mole) acrolein in 40 mL ethanol is added dropwise. The mixture is stirred overnight and the ethanol removed under vacuum. The product was recrystallized from methylene chloride and dried under vacuum. 150 g white crystals were obtained.

(b) 51.63 g triphenylphosphine is melted and dissolved in 100 mL dry dimethylacetamide. The solution is cooled to −5° C. and 41.34 g (0.197 mole) dibromodifluoromethane is added dropwise. 20.0 g (0.0984 mole) of the product of step (a), dissolved in 70 mL methylene chloride, is added, followed by 12.88 g Zn catalyst. The mixture is stirred for 2 h and filtered. The filtrate is separated using 200 mL methylene chloride and 200 mL water. The organic layer is washed twice with water and extracted with 100 mL 5% sodium hydroxide solution, 100 mL 10% HCl, and 200 mL water. The solvent is removed under vacuum to yield N-(4,4-difluoro-3-butenyl)phthalimide.

(c) 51.0 g (0.215 mole) of the product of step (b) is mixed with 250 mL ethanol and 24.11 g hydrazine. After stirring and heating at reflux for 45 min., 71.38 g HCl and 70 mL water are added to the mixture and reflux is continued for 30 min. Solvent is removed under vacuum and the remaining mixture partitioned between 300 mL water and 200 mL methylene chloride. The pH of the water layer is raised to 12 with 50% aqueous sodium hydroxide and the mixture extracted twice with 200 mL methylene chloride. The combined methylene chloride solutions are added to 100 mL 6N HCl and the solvent removed under vacuum. The crude amine salt is added to 30 g sodium hydroxide pellets and the free amine is distilled out. The amine is added to 50 mL 6N HCl and the water removed under vacuum to yield 13.31 g of the title compound, Compound 46, as white crystals.

From Compound 46, the difluoro analogs of the trifluorobuteneamine derivatives made in the preceding examples may be prepared, for example the methyl ester of N-(4,4-difluoro-3-butenyl)glycine hydrochloride (Compound 76).

SYNTHESIS EXAMPLE 22

Synthesis of 5-Hexenoic acid, 5,6,6-trifluoro-, (Compound 104)

(a) In a 1 liter flask under $N_2$ is added 5.5 g (0.226 mole) of Mg turnings and 250 mL anhydrous ether. 40 g (0.212 mole) of 4-bromo-1,1,2-trifluorobutene is added dropwise until a vigorous reflux ensued. The remainder was then added dropwise at a rate to keep the reflux proceeding gently. After the addition was complete, the reaction was stirred 30 min more. The reaction was then cooled to between −30° C. and −50° C. with dry ice/acetone. 4.04 g of CuI was added followed by 8.5 mL (0.017 mole) of condensed ethylene oxide. This was left standing at −30° to −10° C. for 20 min then warmed to room temperature. A reflux started to take place and the reaction was cooled in an ice bath, then at room temperature over 3 days. 200 mL of 10% HCl was then slowly added, followed by 35 mL of conc. HCl, After stirring for 2 h, the precipitate was filtered off. The separated ether layer was washed once with water, once with saturated $NaHCO_3$, once again with water, dried over $MgSO_4$ and removed under vacuum. The residue was distilled twice. A 4.8 g fraction boiling at 58°–59° C. at about 2 mmHg was collected.

(b) 15 mL of Jones Reagent (Fieser and Fieser Vol. 1, Pg. 142) was added dropwise to 3 g (0.019 mole) of the compound prepared in step (a) in 48 mL acetone and kept at approx. 20° C. with an ice bath during the addition. After the addition was complete, the reaction was stirred for 1/2 h longer at room temperature. The chromate salts were separated out by passing the reaction mixture through silica gel. After washing with acetone, the acetone was removed under vacuum. The residue was diluted with water and the product extracted into ether. The ether was washed 3 times with water, dried over $MgSO_4$ and removed under vacuum. The crude product is dissolved in ether and extracted into saturated $NaHCO_3$. The $NaHCO_3$ layer is washed with ether, then acidified with conc. HCl. The desired product is extracted into ether. The ether is washed once with water, dried over $MgSO_4$ and removed under vacuum to yield 1 g of product as a clear liquid.

SYNTHESIS EXAMPLE 23

Synthesis of 3-Butenamide, 3,4,4-trifluoro-N-hydroxy-, (Compound 105)

To 1 g (0.0071 mole) of Compound 44 in 10 mL anhydrous THF is added 1.16 g (0.0071 mole) of carbonyldiimidazole. After 20 min 0.75 g (0.0071 mole) of O-TMS hydroxylamine (Aldrich) was added to the reaction mixture. This was stirred at room temperature for 2 days. The solvent was then removed under vacuum. The residue was taken up in ethyl acetate and washed 2 times with a minimum of 10% HCl. The ethyl acetate was dried over $MgSO_4$ and removed under vacuum. The residue was then stirred for 2 h in methanol. The methanol was removed under vacuum. The residue was sublimed (at about 80° C. at 1–2 mmHg). The sublimed solid was stirred 3 times in ether/pet. ether (solvent decanted off each time); then recrystallized from 30% ethyl acetate/hexane to yield 100 mg of product as a white solid. m.p. 99°–100° C.

SYNTHESIS EXAMPLE 24

Synthesis of 3-Butenoic acid, 3,4,4-trifluoro-, (2,2-dimethyl-1,3-dioxolan-4-yl)methyl ester, (Compound 106)

1.16 g (0.0071 mole) of carbonyldiimidazole is added to 1 g (0.0071 mole) of Compound 44 in 10 mL anhydrous THF. After 20 min 0.94 g (0.0071 mole) of solketal was added and the reaction was stirred at room temperature for 3 days. The solvent is removed under vacuum. The residue is taken up in pet. ether. The pet. ether is washed 4 times with water, dried over $MgSO_4$ and removed under vacuum to yield 0.44 g of the product as a clear liquid.

SYNTHESIS EXAMPLE 25

Synthesis of Benzoic acid, 4-[(3,4,4-trifluoro-3-butenyl)amino]-, methyl ester, (Compound 107)

4.1 g (0.027 mole) of methyl 4-aminobenzoate and 2 g (0.00714 mole) of 3,4,4-trifluoro-3-butene tosylate were heated neat at 130° C. for 4 h. The resulting product was taken up (after cooling) in ethyl acetate. The precipitate was filtered off; the ethyl acetate washed once with water, dried over $MgSO_4$ and removed under vacuum. The crude product was chromatographed by HPLC. (15% ethyl acetate/hexane) to yield 1.48 g of product as a clear liquid which turned to a white solid. m.p. 47°–49° C.

SYNTHESIS EXAMPLE 26

Synthesis of Benzoic acid, 4-[(3,4,4-trifluoro-3-butenyl)amino]-, (Compound 109)

1 g (0.00386 mole) of Compound 107 and 0.15 g (0.00386 mole) of NaOH in 10 mL water and 10 mL ethanol were stirred at room temperature overnight. The solvent was removed under vacuum. Water was added to the residue and washed once with ether. The water layer was then acidified with conc. HCl. The resulting precipitate was filtered, washed with water and dried to yield 0.33 g of the desired product as a white solid. m.p. 149°–151° C.

SYNTHESIS EXAMPLE 27

Synthesis of Acetamide, 2-[(3,4,4-trifluoro-3-butenyl)amino]-, monohydrochloride (Compound 108)

3.9 g (0.028 mole) of bromacetamide was added slowly to 15 g (0.093 mole) of Compound 1, 9.6 g (0.093 mole) of triethylamine and 180 mL THF and stirred overnight at room temperature. The precipitate was filtered off and the solvent removed from the filtrate. The residue was stirred in ether/methylene chloride twice and each time the precipitate was filtered off. Excess HCl gas was then bubbled into the solution; the resulting precipitate was filtered, washed with ether and dried under vacuum. The product was dissolved in water and the water solution washed twice with ether. The water was removed under vacuum and the resulting crude product was recrystallized from ethanol to yield 2.39 g of product as a white solid. m.p. 198°–200° C.

SYNTHESIS EXAMPLE 28

Synthesis of 7,8,8-trifluoro-V-octenoic acid (Compound 84)

A solution of 4-bromobutyric acid (8.35 g, 0.05 mole) in anhydrous THF (100 mL) is treated dropwise with methyl magnesium chloride (0.051 mole, 17 mL of 3M solution in THF) at −25° C. with stirring in 15 min. The solution is stirred for an additional 15 min at 0° C. and treated with dilithium tetrachlorocuprate (0.002 mole, 20 mL of 0.1 M solution in THF) followed by 3,4,4-trifluoro-3-butenyl magnesium bromide (0.0565 mole, prepared separately from 3,4,4-trifluoro-3-butenyl bromide and magnesium turnings in THF). The mixture is stirred at 0° C. for 2 h and at room temperature for overnight. The solution is then poured in 400 mL of ether and 150 mL of 10% aqueous sulfuric acid. The ether layer is extracted with 10% NaOH (2×50 mL). The aqueous layer is washed with ether, acidified with conc. HCl, and extracted with ether (3×100 mL). The ether extract is dried, concentrated, and the residue distilled under vacuum to give 4.1 g of the desired product as a colorless liquid, a 42% yield. b.p. 125°–127° C./10 Torr.

SYNTHESIS EXAMPLE 29

Synthesis of 3,4,4-trifluoro-3-butenoic acid, phenylmethyl ester (Compound 113)

A solution of 3,4,4-trifluoro-3-butenoyl chloride (2.8 g, 0.0176 mole) and benzyl alcohol (0.9 g, 0.0083 mole) in 20 mL dichloromethane is heated at reflux for 40 h. The solution is cooled to room temperature, diluted with dichloromethane (15 mL), washed successively with 5% sodium bicarbonate, water and brine, and dried. Evaporation of the solvent gave 1.75 g of analytically pure product as a pale yellow oil, a 92% yield.

SYNTHESIS EXAMPLE 30

Synthesis of 3,4,4-trifluoro-3-butenoic acid, 4-nitrophenyl ester (Compound 117)

A solution of 4-nitrophenol (1.10 g, 0.0079 mole) and 3,4,4-trifluoro-3-butenoyl chloride (1.85 g, 0.0116 mole) in dry ether (15 mL) is treated dropwise with triethylamine (1.01 g, 0.01 mole) at −78° C. with stirring. The mixture is stirred at −78° C. for 10 min and allowed to reach room temperature. The reaction mixture is diluted with ether (20 mL), stirred with 15 mL of 2 N HCl. The organic layer is successively washed with water, 5% sodium bicarbonate, brine, and dried. The dark brown residue obtained after evaporation of the solvent was purified by passing through a short column of silica gel to give 1.9 g of the product as a brown solid, a 91% yield. m.p. 58°–62° C.

SYNTHESIS EXAMPLE 31

Synthesis of 3,4,4-trifluoro-3-butenoic acid, 2-(3,4,4-trifluoro-1-oxo-3-butenyl)hydrazide (Compound 120)

A solution of 3,4,4-trifluoro-3-butenoyl chloride (2.4 g, 0.0151 mole) in dry ether (20 mL) is treated dropwise with anhydrous hydrazine (0.48 g, 0.15 mole) with stirring at −78° C. The mixture is allowed to reach room temperature and the white precipitate is filtered and dissolved in ethyl acetate. The ethyl acetate solution is washed with 5% sodium bicarbonate and dried. Evaporation of the solvent gave 1.1 g of the desired product as a white solid, a 47% yield. m.p. 191°–193° C.

SYNTHESIS EXAMPLE 32

Synthesis of 3,4,4-trifluoro-3-butenethioic acid, S-octyl ester (Compound 121)

A mixture of 3,4,4-trifluoro-3-butenoyl chloride (1.7 g, 0.0107 mole) and 1-octanethiol (0.72 g, 0.0049 mole) is heated at 70° C. for 12 h. The crude product is purified by passing through a short column of silica gel to give 1.2 g of the desired product as a pale yellow oil, a 91% yield.

SYNTHESIS EXAMPLE 33

Synthesis of 3,4,4-trifluoro-3-butenethioic acid, S-2-aminoethyl ester, hydrochloride (Compound 127)

A mixture of 3,4,4-trifluoro-3-butenoyl chloride (2.5 g, 0.0158 mole) and 2-aminoethanethiol hydrochloride (1.14 g, 0.010 mole) is slowly heated to reflux for 15 min. The mixture is cooled to room temperature and treated with dry ether and filtered. The product is recrystallized from absolute ethanol to give 0.8 g of the title compound as a off-white solid, a 34% yield. m.p. 95°–115° C.

SYNTHESIS EXAMPLE 34

Synthesis of 3,4,4-trifluoro-3-butenoic acid, 2-aminoethyl ester, monohydrochloride (Compound 130)

A solution of 3,4,4-trifluoro-3-butenoyl chloride (1.97 g, 0.0124 mole) and N-t-Boc-aminoethanol (1.61 g, 0.010 mole) in dry ether (20 mL) is treated with triethylamine (1.25 g, 0.0124 mole) at −78° C. with stirring. The mixture is stirred for 30 min and allowed to reach room temperature and poured in 20 mL of water. The ether layer is successively washed with 5% sodium bicarbonate and brine and dried. The ether solution is saturated with dry HCl gas and stirred at room temperature for 30 min. The precipitate is filtered and dried to give 1.6 g of the title compound as a white solid, a 77% yield. m.p. 94°–100° C.

SYNTHESIS EXAMPLE 35

Synthesis of Oxo[(3,4,4-trifluoro-3-butenyl)amino]oxoacetic acid, methyl ester (Compound 142)

A solution of 3,4,4-trifluoro-3-butene-1-amine (12.5 g, 0.1 mole) and triethylamine (10.1 g, 0.1 mole) in dry ether (200 mL) is treated with methyl oxalyl chloride (12.3 g, 0.1 mole in 30 mL ether) dropwise at 0° C. with stirring. The mixture is stirred at room temperature for 30 min and treated with 30 mL water. The organic layer is successively washed with 2N HCl, water, 5% sodium bicarbonate, and brine and dried. The residue obtained after evaporation of the solvent is purified by distillation to give 16.42 g of the desired product as a white solid, a 78% yield. m.p. 33°–34° C.

SYNTHESIS EXAMPLE 36

Synthesis of N-(3,4,4-trifluoro-3-butenyl)ethanediamide (Compound 143)

A solution of Compound 142 (5.0 g, 0.0237 mole) in methanol (50 mL) is saturated with dry gaseous ammonia at room temperature. The precipitate is filtered, washed with methanol and dried to give 3.16 g of the title compound as a white solid, a 68% yield. m.p. 190°–220° C.

SYNTHESIS EXAMPLE 37

Synthesis of N-[(3,4,4-trifluoro-3-butenyl)amino]oxoacetic acid, hydrazide (Compound 144)

A solution of Compound 142 (4.22 g, 0.02 mole) in absolute ethanol (50 mL) is treated with hydrazine monohydrate (1.6 g, 0.032 mole) with stirring. The precipitate is filtered, washed with ethanol and dried to give 2.54 g of the title compound as a white solid, a 60% yield. m.p. 145°–200° C.

SYNTHESIS EXAMPLE 38

Synthesis of [(3,4,4-trifluoro-3-butenyl)amino]oxoacetic acid, (Compound 145)

A solution of Compound 142 (3.16 g, 0.015 mole) in methanol (25 mL) is treated with a solution of NaOH (0.8 g, 0.02 mole) in water (5 mL). The solution is stirred at room temperature for 30 min and concentrated. The residue is dissolved in water (20 mL) and extracted with dichloromethane (2×30 mL). The aqueous layer is acidified with conc. HCl and extracted with ethyl acetate. The organic layer is dried and evaporated to give 0.75 g of the title compound as a white solid, a 25% yield. m.p. 95°–100° C.

SYNTHESIS EXAMPLE 39

Synthesis of N-butyl-3,4,4-trifluoro-3-butenamide (Compound 103)

2.5 g (0. 0158 mole) 3,4,4-trifluoro-3-butenoyl chloride is added to a mixture of water (15 mL), dichloromethane (15 mL) and n-butyl amine (2.34 g, 0.032 mole) with stirring at 0° C. After stirring for 30 min, the organic layer is successively washed with 2N HCl, water, 5% sodium bicarbonate and brine, and dried. Evaporation of the solvent gave 2.85 g of title compound as a white solid, a 92% yield. m.p. 34°–36° C.

SYNTHESIS EXAMPLE 40

Synthesis of 3-[(3,4,4-trifluoro-1-oxo-3-butenyl)amino]benzoic acid (Compound 128)

2.2 g (0. 0139 mole) 3,4,4-trifluoro-3-butenoyl chloride is added to a mixture of 3-aminobenzoic acid (1.37 g, 0.01 mole), sodium bicarbonate (0.84 g, 0.01 mole), water (20 mL) and dichloromethane (20 mL) with stirring at 0° C. After stirring for 15 min at room temperature, the mixture is diluted with ethyl acetate (100 mL) and water (50 mL). The organic layer is washed with 2N HCl and brine, and dried. The residue obtained after evaporation of the solvent is triturated with dry ether and filtered to give 1.8 g of the title compound as a light pink solid, a 69% yield. m.p. 252°–255° C.

SYNTHESIS EXAMPLE 41

Synthesis of 2,4-dihydro-4-[[(3,4,4-trifluoro-3-butenyl)amino]methylene]-3H-pyrazol-3-one (Compound 131)

A solution of 3,4,4-trifluoro-3-butene-1-amine (2.25 g, 0. 018 mole) and 4,5-dihydro-5-oxo-1H-pyrazole- 4-carboxaldehyde (1.12 g 0.01 mole) in absolute ethanol (30 mL) is heated at reflux for 15 min. The solution is concentrated and the residue is recrystallized from ether/dichloromethane to give 1.49 g of the title compound as an yellow solid, a 68% yield. m.p. 126°–130° C.

SYNTHESIS EXAMPLE 42

Synthesis of 3,4,4-Trifluoro-3-butenoyl chloride (Compound 101)

To 46.7 g (334 mmol) of the freshly distilled 3,4,4-trifluoro-3-butenoic acid (Compound 44) in 100 mL dichloromethane containing 2 drops of dimethylformamide at 0° C. was added 31 mL (355 mmol) of oxalyl chloride over 5 min. The mixture was stirred at 0° C. and was allowed to warm to ambient temperature overnight. The mixture was fractionally distilled rapidly at ambient pressure through a 20 cm Vigreux column fitted with a short path distillation head. The pure acid chloride 31.8 g (60% yield) was obtained as a colorless liquid, b.p. 90°–97° C. (oil bath temperature 130° C). Slow decomposition took place on storage at room temperature.

The other acid halides, for example, 3,4,4-trifluoro-3-butenoyl bromide, may be prepared from Compound 101 or by a similar method from Compound 44, As would be obvious to one of ordinary skill in the art, other activated acid functionalities, such as symmetrical or asymmetrical anhydrides or the imidazole carbonyl, can be prepared from the acids or acid chlorides of the present invention and may be useful in the pest control methods herein described.

SYNTHESIS EXAMPLE 43

Synthesis of Glycine, N-(3,4,4-trifluoro-1-oxo-3-butenyl)-, 1,1-dimethylethyl ester (Compound 90)

To 5.6 g (66.7 mmol) of sodium bicarbonate suspended in 40 mL water at 0° C. was added 20 mL dichloromethane followed by 5.6 g (33.4 mmol) of tert-butyl glycinate hydrochloride. To the mixture was added 5.25 g (33.2 mmol) of 3,4,4-trifluoro-3-butenoyl chloride (Compound 101) in several portions over five min. The mixture was stirred for 30 min at 0° C. and the phases were separated. The aqueous phase was extracted with dichloromethane and the organic phases were combined, diluted with ether, and washed with saturated aqueous sodium chloride. The solution was dried over magnesium sulfate and concentrated. The residue was kugelrohr distilled at 90°–95° C. (0.1 mmHg) to give 6.85 g (82 %) of a colorless crystalline solid. m.p. 52°–54° C.

SYNTHESIS EXAMPLE 44

Synthesis of Glycine, N-(3,4,4-trifluoro-1-oxo-3-butenyl-, (Compound 91)

To 7.7 g (30.4 mmol) of glycine, N-(3,4,4-trifluoro-1-oxo-3-butenyl)-, 1,1-dimethylethyl ester (Compound 90) was added 8 mL trifluoroacetic acid. The solution was stirred at ambient for 24 h and was concentrated. The residue was recrystallized from ethyl acetate/ether to give 1.7 g of colorless needles. m.p. 115°–116° C. The mother liquors were concentrated and crystallized from ethyl acetate/ether to give additional material totaling 4.4 g (73%).

SYNTHESIS EXAMPLE 45

Synthesis of 3-butenamide, N-(2-aminoethyl)-3,4,4-trifluoro, hydrochloride-, (Compound 96)

(a) To 3.5 g (21.9 mmol) of carbamic acid, (2-aminoethyl)-,1,1-dimethylethyl ester [prepared as described in Krapcho, A. P., Kuell, C. S. *Synthetic Communications,* 1990, 20, 2559–2564] in 40 mL dichloromethane at 0° C. was added 15 mL water and 2.02 g (24 mmol) of sodium bicarbonate. The mixture was stirred for 5 min and 3.46 g (21.9 mmol) of 3,4,4-trifluoro-3-butenoyl chloride (Compound 101) was added over 2 min. A white precipitate formed during the addition. The mixture was allowed to warm to ambient and 150 mL dichloromethane was added to dissolve the product. The phases were separated and the organic phase was stirred with anhydrous sodium sulfate, filtered, and concentrated. The residue was recrystallized from ethyl acetate to give 4.25 g (69%) of a white solid. m.p. 123°–124° C.

(b) To 2.45 g (8.69 mmol) of the carbamate prepared in step (a) in 15 mL methanol at ambient was added a solution of HCl in methanol prepared by the addition of 0.68 mL (6.5 mmol) acetyl chloride to 5 mL methanol with swirling. The mixture was stirred at ambient for 3 h and was concentrated. Recrystallization of the residue from 2-propanol/ethyl acetate gave about 200 mg of the salt as a white powder, m.p. 138°–146° C. A second crop of pure hydrochloride salt was obtained as colorless plates. m.p. 145°–147° C. The yield of both crops was 470 mg (33%).

SYNTHESIS EXAMPLE 46

Synthesis of 7-Octen-1-amine, 7,8,8-trifluoro-, monohydrochloride (Compound 59)

(a) A 1-liter 4-necked flask was charged with magnesium turnings (15.4 g, 0.635 mole) and anhydrous THF (100 mL) under $N_2$. A few crystals of iodine were added and the mixture was heated until the iodine color disappeared. A solution of 1-bromo-3,4,4-trifluoro-3-butene (100 g, 0.529 mole) in anhydrous THF (500 mL) was added dropwise at a rate such that THF refluxed gently. After the addition was complete (about 1 h), the solution was heated at reflux for 30 min. The solution was cooled to about 30° C. and transferred to a dropping funnel under $N_2$ pressure using a cannula, leaving the unreacted magnesium turnings in the flask.

(b) A 3-liter, 4-necked flask was charged with 1,4-dibromobutane (114.4 g, 0.530 mole, 63.3 mL), dilithium tetrachlorocuprate (80 mL of 0.1M solution in THF, 8.0 mmol) and anhydrous THF (250 mL). The mixture was cooled to about 5° C. and treated dropwise with the Grignard reagent prepared in step (a), with stirring at 5–°10° C. The addition was completed in 30 min. The mixture was then stirred at 5°–10° C. for 3 h and at room temperature overnight. The reaction mixture was diluted with ether (1200 mL), cooled in ice-water bath and treated slowly with 5% sulfuric acid (500 mL). The ether layer was successively washed with 5% sulfuric acid (300 mL), water (200 mL), sat. $NaHCO_3$ (200 mL), brine (200 mL) and dried over $MgSO_4$. The solvent was evaporated and the residue was distilled under vacuum to give 100.2 g of crude product as a colorless oil. b.p. 85°–100° C. at 35 mmHg. This fraction was dissolved in dimethylsulfoxide (DMSO) (400 mL, anhydrous) and treated with $NaN_3$ (88.4 g, 1.36 mole) with stirring at room temperature. After a few minutes a thick white crystalline material was formed and an additional 200 mL DMSO was added and stirred vigorously for 1 h. The mixture was then treated with 600 mL water and extracted into ether (2×600 mL). The ether extract was washed with water (3×300 mL), brine (300 mL) and dried over $MgSO_4$. Evaporation of the solvent gave 77.0 g of a pale yellow oil. This oil was dissolved in 400 mL Of DMSO and treated in one portion with triphenylphosphine (225 g, 0.858 mole) with stirring. The reaction mixture was cooled in ice-water bath until the exotherm ceased, and was stirred at room temperature for 5 h. 750 mL of conc. ammonium hydroxide was then added and the mixture stirred overnight. The mixture was diluted with ether (1500 mL) and the precipitate was filtered off. The filtrate was washed with water and the ether layer was extracted with 10% HCl. The aqueous layer was then back extracted with dichloromethane and concentrated under vacuum. The residue was treated with 60% toluene/absolute ethanol and evaporated to remove traces of water. The residue (10.1 g) appeared as a pale yellow solid, an 8.7% yield.

SYNTHESIS EXAMPLE 47

Synthesis of 5-Hexen-1-amine, 5,6,6-trifluoro-, monohydrochloride (Compound 74)

(a) To magnesium turnings (26.7 g, 1.1 mole) in dry ether (500 mL) were added a few crystals of iodine. The mixture was heated until the ether refluxed and 4-bromo-1,1,2-trifluoro-1-butene (189 g, 1.0 mole) in dry ether (400 mL)

was added dropwise with stirring at a rate such that ether refluxed gently. The addition took 1.5 h. After the addition was complete, 200 mL dry ether was added and the mixture heated at reflux for 30 min. The mixture was cooled to about −30° C. and CuI (19.0 g, 0.1 mole) was added. Ethylene oxide, condensed in a dry ice-acetone cooled dropping funnel (55 g, 1.25 mole), was added dropwise with stirring at −30° C. in approx. 30 min. Then the mixture was allowed to reach room temperature overnight. The mixture was then cooled to 0° C., treated slowly with 500 mL 10% HCl and 150 mL conc. HCl, and filtered. The layers were separated and the aqueous layer was extracted with ether. The combined ether extracts were washed with sat. NaHCO$_3$, followed by brine, and dried over MgSO$_4$. After careful evaporation of the solvent, 195 g of red colored oil was obtained. Distillation under reduced pressure gave 155 g of colorless oil. b.p. 90°–100° C./80–75 mmHg. The product was then treated with 1.5 L of hexanes and washed four times with water. The hexane layer was dried over anhydrous Na$_2$SO$_4$ and concentrated to give 100 g of a clear oil, which was distilled under vacuum to give 95 g of 5,6,6-trifluoro-5-hexenol as a clear oil, a 61.7 % yield.

(b) A solution of mesyl chloride (46.5 mL, 600 mmol) in dichloromethane (250 mL) was added dropwise to a solution of the alcohol prepared as in step (a) (77.0 g, 500 mmol) and triethylamine (104.5 mL, 750 mmol) in dichloromethane (750 mL) at −25° C. with stirring. Stirring was continued for 30 min at −20° C. The mixture was then treated with 10% HCl (300 mL) and the organic layer was washed with 10% HCl (200 mL) followed by sat. NaHCO$_3$ (200 mL), brine (200 mL) and dried over MgSO$_4$. Evaporation of the solvent gave 116 g of yellow oil. This was dissolved in DMSO (400 mL) and reacted with NaN$_3$ (65 g, 1000 mmol) at room temperature overnight. Triphenylphosphine (157.4 g, 600 mmol) was then added to the reaction mixture with cooling. The mixture was stirred at room temperature for 5 h, and conc. ammonium hydroxide was added. The mixture was stirred at room temperature overnight. The reaction mixture was then diluted with ether (1500 mL) and extracted with water. The precipitate was filtered off, and the ether layer was washed with water and extracted with 10% HCl. The aqueous layer was back extracted three times with dichloromethane and concentrated in a rotary evaporator under vacuum to yield the desired product as a pale yellow solid, 74.6 g, a 78.7% yield.

Using methods and starting materials as generally described above and illustrated in the preceding examples the following compounds were made:

| Example Compound # | Name | Structure | | Analysis (%) Calc'd | Found |
|---|---|---|---|---|---|
| 1 | 3-buten-1-amine,-3,-4,-4-trifluoro-,-monohydrochloride MP: 185.0–190.0 | $F_2C=CF-(CH_2)_2-NH_2 \cdot HCl$ | C<br>H<br>Cl<br>F<br>N | 29.74<br>4.37<br>21.94<br>35.28<br>8.67 | 29.78<br>4.36<br><br><br>8.64 |
| 2 | 3-buten-1-amine,-3,-4,-4-trifluoro-,-monohydrobromide MP: 228.0–230.0 | $F_2C=CF-(CH_2)_2-NH_2 \cdot HBr$ | C<br>H<br>Br<br>F<br>N | 23.32<br>3.42<br>38.79<br>27.67<br>6.80 | 23.28<br>3.42<br><br><br>6.74 |
| 3 | 3-buten-1-amine,-3,-4,-4-trifluoro-,-monohydroiodide MP: 217.0–219.0 | $F_2C=CF-(CH_2)_2-NH_3^+ I^-$ | C<br>H<br>F<br>I<br>N | 18.99<br>2.79<br>22.53<br>50.16<br>5.54 | 18.97<br>2.74<br><br><br>5.49 |
| 4 | acetic acid,-compd. with 3,-4,-4-trifluoro-3-buten-1-amine (1:1)- MP: | $F_2C=CF-(CH_2)_2-NH_3^+ \; CH_3-C(=O)-O^-$ | C<br>H<br>F<br>N | 38.92<br>5.44<br>30.79<br>7.57 | 37.00<br>5.42<br><br>5.95 |
| 5 | 3-buten-1-amine,-3,-4,-4-trifluoro- MP: | $F_2C=CF-(CH_2)_2-NH_2 + .7 \; H_2SO_4$ | C<br>H<br>F<br>N<br>S | 18.31<br>3.38<br>21.72<br>5.34<br>17.11 | 24.74<br>4.01<br><br>7.12<br>11.03 |
| 6 | 3-buten-1-amine,-3,-4,-4-trifluoro- MP: 157.0–159.0 | $F_2C=CF-(CH_2)_2-NH_2 + .77 \; HO-C(=O)-C(=O)-OH$ | C<br>H<br>F<br>N | 32.24<br>3.47<br>21.61<br>5.31 | 34.24<br>4.17<br><br>7.22 |
| 7 | 1,-2,-3-propanetricarboxylic acid,-2-hydroxy-,-compd. with 3,-4,-4-trifluoro-3-buten-1-amine (1:3)- MP: 118.0–120.0 | $O^--C(=O)-CH_2-C(OH)(C(=O)-O^-)-CH_2-C(=O)-O^- \; +3 \; F_2C=CF-(CH_2)_2-NH_3^+$ | C<br>H<br>F<br>N | 38.10<br>4.62<br>30.14<br>7.41 | 38.19<br>4.56<br><br>7.35 |

-continued

| Ex-ample Compound # | Name | Structure | Analysis (%) Calc'd | Found |
|---|---|---|---|---|
| 8 | glycine,-N-(3,-4,-4-trifluoro-3-butenyl)-,-methyl ester,-monohydrochloride MP: 190.0–191.0 | $F_2C{=}CF{-}(CH_2)_2{-}NH{-}CH_2{-}\underset{\underset{O}{\parallel}}{C}{-}O{-}CH_3$ · HCl | C 35.99<br>H 4.75<br>Cl 15.18<br>F 24.40<br>N 6.00 | 36.04<br>4.78<br><br><br>5.97 |
| 9 | glycine,-N-(3,-4,-4-trifluoro-3-butenyl)-,-monohydrochloride MP: 187.0–189.0 | $F_2C{=}CF{-}(CH_2)_2{-}NH{-}CH_2{-}\underset{\underset{O}{\parallel}}{C}{-}OH$ · HCl | C 32.82<br>H 4.13<br>Cl 16.14<br>F 25.96<br>N 6.38 | 32.79<br>4.15<br><br><br>6.35 |
| 10 | valine,-N-(3,-4,-4-trifluoro-3-butenyl)-,-monohydrochloride MP: 207.0–213.0 | .HCl<br>$F_2C{=}CF{-}(CH_2)_2{-}NH{-}CH{-}\underset{\underset{O}{\parallel}}{C}{-}OH$<br>$\quad\quad\quad\quad\quad\quad\quad\quad\quad CH_3{-}CH{-}CH_3$ | C 41.31<br>H 5.78<br>Cl 13.55<br>F 21.78<br>N 5.35 | 41.44<br>5.78<br><br><br>5.39 |
| 11 | dl-alanine,-N-(3,-4,-4-trifluoro-3-butenyl)-,-hydrochloride MP: 133.0–135.0 | $\quad\quad\quad\quad\quad\quad\quad\quad CH_3$<br>$F_2C{=}CF{-}(CH_2)_2{-}NH{-}CH{-}\underset{\underset{O}{\parallel}}{C}{-}OH$<br>.HCl<br>(DL) | C 35.99<br>H 4.75<br>Cl 15.18<br>F 24.40<br>N 6.00 | 35.89<br>4.73<br><br><br>5.95 |
| 12 | L-alanine,-N-(3,-4,-4-trifluoro-3-butenyl)-,-monohydrochloride MP: 98.0–102.0 | .HCl  CH₃<br>$F_2C{=}CF{-}(CH_2)_2{-}NH\blacktriangleright C\blacktriangleleft\underset{\underset{O}{\parallel}}{C}{-}OH$<br>$\quad\quad\quad\quad\quad\quad\quad\quad\quad H$<br>S - ISOMER | C 35.99<br>H 4.75<br>Cl 15.18<br>F 24.40<br>N 6.00 | |
| 13 | l)-alanine,-N-(3,-4,-4-trifluoro-3-butenyl)-,-monohydrochloride MP: 98.0–102.0 | .HCl  H<br>$F_2C{=}CF{-}(CH_2)_2{-}NH\blacktriangleright C\blacktriangleleft\underset{\underset{O}{\parallel}}{C}{-}OH$<br>$\quad\quad\quad\quad\quad\quad\quad\quad\quad CH_3$<br>R - ISOMER | C 35.99<br>H 4.75<br>Cl 15.18<br>F 24.40<br>N 6.00 | |
| 14 | L-aspartic acid,-N-(3,-4,-4-trifluoro-3-butenyl)-,-mixt. with n-(3,--4,-4-trifluoro-3-butenyl-L-aspartic acid,-monohydrochloride MP: | .HCl<br>$\quad\quad O\quad\quad NH{-}(CH_2)_2{-}CF{=}CF_2$<br>$HO{-}\underset{\parallel}{C}\blacktriangleright \underset{H}{C}\blacktriangleleft CH_2{-}\underset{\underset{O}{\parallel}}{C}{-}OH\quad +$<br>$\quad\quad\quad\quad\quad\quad\quad\quad\quad\quad 1.0$<br><br>$\quad\quad O\quad\quad NH{-}(CH_2)_2{-}CF{=}CF_2$<br>$HO{-}\underset{\parallel}{C}\blacktriangleright \underset{H}{C}\blacktriangleleft CH_2{-}\underset{\underset{O}{\parallel}}{C}{-}OH$<br>$\quad\quad\quad\quad\quad\quad\quad\quad\quad\quad 0.8$<br>(L) | C 37.93<br>H 4.11<br>Cl 4.66<br>F 22.50<br>N 5.53 | 36.60<br>4.19<br><br><br>5.29 |
| 15 | beta-alanine,--N-(3,-4,-4-trifluoro-3-butenyl)-,-methyl ester,-monohydrochloride MP: 172.0–175.0 | $F_2C{=}CF{-}(CH_2)_2{-}NH{-}(CH_2)_2{-}\underset{\underset{O}{\parallel}}{C}{-}O{-}CH_3$ · HCl | C 38.80<br>H 5.29<br>Cl 14.32<br>F 23.02<br>N 5.66 | 38.42<br>5.29<br><br><br>5.81 |
| 16 | beta-alanine,-N-(3,-4,-4-trifluoro-3-butenyl)-,-monohydrochloride MP: 74.0–75.0 | $F_2C{=}CF{-}(CH_2)_2{-}NH{-}(CH_2)_2{-}\underset{\underset{O}{\parallel}}{C}{-}OH$ · HCl | C 35.99<br>H 4.75<br>Cl 15.18<br>F 24.40<br>N 6.00 | 35.37<br>4.80<br><br><br>5.95 |

-continued

| Example Compound # | Name | Structure | Analysis (%) Calc'd | Found |
|---|---|---|---|---|
| 17 | 3-buten-1-amine,-3,-4,-4-trifluoro-N-methyl-,-monohydrochloride MP: 120.0–122.0 | F₂C=CF—(CH₂)₂—NH—CH₃ · HCl | C 34.20<br>H 5.17<br>Cl 20.19<br>F 32.46<br>N 7.98 | 34.30<br>5.17<br><br><br>7.87 |
| 18 | butanoic acid,-2-[(3,-4,-4-trifluoro-3-butenyl)-amino]-,-methyl ester,-monohydrochloride,-(+−)- MP: 104.0–105.0 | F₂C=CF—CH₂—CH₂—NH—CH(CH₂CH₃)—C(=O)—O—CH₃ · HCl (DL) | C 41.31<br>H 5.78<br>Cl 13.55<br>F 21.78<br>N 5.35 | 41.45<br>5.73<br><br><br>5.30 |
| 19 | propanamide,-2-[(3,-4,-4-trifluoro-3-butenyl)-amino]-,-monohydrochloride,-(+−)- MP: 148.0–149.0 | F₂C=CF—(CH₂)₂—NH—CH(CH₃)—C(=O)—NH₂ · HCl (DL) | C 36.14<br>H 5.20<br>Cl 15.24<br>F 24.50<br>N 12.04 | 36.25<br>5.25<br><br><br>12.12 |
| 20 | D-alanine,-N-(3,-4,-4-trifluoro-3-butenyl)-,-phenylmethyl ester,-monohydrochloride MP: 133.0–135.0 | F₂C=CF—(CH₂)₂—NH—C(CH₃)(H)—C(=O)—O—CH₂—C₆H₅ · HCl R-ISOMER | C 51.94<br>H 5.29<br>Cl 10.95<br>F 17.61<br>N 4.33 | 52.03<br>5.31<br><br><br>4.31 |
| 21 | ethanediamide,-N,-n'-bis(3,-4,-4-trifluoro-3-butenyl)- MP: 139.0–141.0 | F₂C=CF—(CH₂)₂—NH—C(=O)—C(=O)—NH—(CH₂)₂—CF=CF₂ | C 39.48<br>H 3.31<br>F 37.47<br>N 9.21 | 39.58<br>3.31<br><br>9.17 |
| 22 | butanoic acid,-4-oxo-4-[(3,-4,-4-trifluoro-3-butenyl)-amino]- MP: 64.0–66.0 | F₂C=CF—(CH₂)₂—NH—C(=O)—(CH₂)₂—C(=O)—OH | C 42.67<br>H 4.48<br>F 25.31<br>N 6.22 | 42.76<br>4.47<br><br>6.18 |
| 23 | phenol,-4-nitro-2-[[(3,-4,-4-trifluoro-3-butenyl)-imino]-methyl]- MP: 96.0–98.0 | F₂C=CF—(CH₂)₂—N=CH—(2-OH,4-NO₂-C₆H₃) | C 48.18<br>H 3.31<br>F 20.79<br>N 10.22 | 48.22<br>3.33<br><br>10.24 |
| 24 | phenol,-2,-4-dichloro-6-[[(3,-4,-4-trifluoro-3-butenyl)-imino]-methyl]- MP: 38.0–40.0 | F₂C=CF—(CH₂)₂—N=CH—(2-OH,3,5-Cl₂-C₆H₂) | C 44.32<br>H 2.71<br>Cl 23.79<br>F 19.12<br>N 4.70 | 43.97<br>2.65<br><br><br>4.55 |
| 25 | benzenamine,-N,-N-dimethyl-4-[[(3,-4,-4-trifluoro-3-butenyl)-imino]-methyl]-,-monohydrochloride MP: 162.0–164.0 | (4-(CH₃)₂N-C₆H₄)—CH=N—(CH₂)₂—CF=CF₂ · HCl | C 53.34<br>H 5.51<br>Cl 12.11<br>F 19.47<br>N 9.57 | 53.30<br>5.51<br><br><br>9.56 |

| Example Compound # | Name | Structure | Analysis (%) Calc'd | Found |
|---|---|---|---|---|
| 26 | 1,-3,-5,-7-tetra-azatricyclo|3.3.1.1-(superscript 3,-superscript 7)-|-decane,-1-(3,-4,-4-trifluoro-3-butenyl)-,-bromide MP: 140.0 | [structure: tetraazatricyclodecane N+—(CH$_2$)$_2$—CF=CF$_2$ Br$^-$] | C 36.49<br>H 4.90<br>Br 24.28<br>F 17.32<br>N 17.02 | 35.80<br>5.03<br><br><br>18.26 |
| 27 | 3-buten-1-amine,-3,-4,-4-trifluoro-N-hydroxy-,-monohydrochloride MP: | F$_2$C=C(F)—(CH$_2$)$_2$—NH—OH · HCl | C 27.06<br>H 3.97<br>Cl 19.97<br>F 32.10<br>N 7.89 | 27.21<br>3.98<br><br><br>7.84 |
| 28 | benzoic acid,-2-(3,-4,-4-trifluoro-3-butenyl)-hydrazide MP: 74.0–76.0 | Ph—C(=O)—NH—NH—(CH$_2$)$_2$—CF=CF$_2$ | C 54.10<br>H 4.54<br>F 23.34<br>N 11.47 | 54.15<br>4.56<br><br>11.48 |
| 29 | hydrazine,-(3,-4,-4-trifluoro-3-butenyl)-,-monohydrochloride MP: | F$_2$C=CF—(CH$_2$)$_2$—NH—NH$_2$·HCl | C 27.21<br>H 4.57<br>Cl 20.08<br>F 32.28<br>N 15.87 | 26.53<br>4.52<br><br><br>15.57 |
| 30 | guanidine,-N-(3,-4,-4-trifluoro-3-butenyl)-,-monohydrochloride MP: | F$_2$C=CF—(CH$_2$)$_2$—NH—C(=NH)—NH$_2$·HCl | C 29.50<br>H 4.46<br>Cl 17.41<br>F 28.00<br>N 20.64 | 29.59<br>4.66<br><br><br>20.66 |
| 31 | 1-butene,-1,-1,-2-trifluoro-4-nitro- MP: | F$_2$C=C(F)—(CH$_2$)$_2$—NO$_2$ | C 30.98<br>H 2.60<br>F 36.75<br>N 9.03 | 31.86<br>2.62<br><br>8.36 |
| 32 | urea,-(3,-4,-4-trifluoro-3-butenyl)- MP: 86.0–88.0 | F$_2$C=CF—(CH$_2$)$_2$—NH—C(=O)—NH$_2$ | C 35.72<br>H 4.20<br>F 33.90<br>N 16.66 | 35.82<br>4.23<br><br>16.65 |
| 33 | benzene-sulfonamide,-N-(3,-4,-4-trifluoro-3-butenyl)-4-(trifluoromethyl)- MP: 68.0–70.0 | F$_2$C=C(F)—(CH$_2$)$_2$—NH—SO$_2$—C$_6$H$_4$—CF$_3$ | C 39.64<br>H 2.72<br>F 34.21<br>N 4.20<br>S 9.62 | 39.71<br>2.74<br><br>4.24<br> |
| 34 | carbamic acid,-|1-methyl-2-oxo-2-|(3,-4,-4-trifluoro-3-butenyl)-amino|-ethyl|,-1,-1-dimethylethyl ester MP: 78.0–79.0 | F$_2$C=C(F)—(CH$_2$)$_2$—NH—C(=O)—CH(CH$_3$)—NH—C(=O)—O—C(CH$_3$)$_3$ L-ISOMER | C 48.64<br>H 6.46<br>F 19.24<br>N 9.45 | 48.70<br>6.46<br><br>9.46 |
| 35 | propanamide,-2-amino-N-(3,-4,-4-trifluoro-2-butenyl)-,-monohydrochloride MP: 164.0–166.0 | F$_2$C=C(F)—(CH$_2$)$_2$—NH—C(=O)—CH(CH$_3$)—NH$_2$·HCl L-ISOMER | C 36.14<br>H 5.20<br>Cl 15.24<br>F 24.50<br>N 12.04 | 36.28<br>5.22<br><br><br>12.06 |

-continued

| Ex-ample Com-pound # | Name | Structure | Analysis (%) Calc'd | Found |
|---|---|---|---|---|
| 36 | asparagine,-n(superscript 2)-(3,-4,-4-trifluoro-3-butenyl)-<br>MP: 167.0–169.0 | $F_2C=C(F)-(CH_2)_2-NH-C(=O)-(CH_2)_2-C(H)(NH_2)-C(=O)-OH \cdot .75\,HCl$<br>L - ISOMER | C 38.39<br>H 4.92<br>Cl 9.44<br>F 20.24<br>N 9.95 | 38.43<br>4.86<br><br><br>9.94 |
| 37 | acetamide,-2-amino-N-(3,-4,-4-trifluoro-3-butenyl)-,-monohydrochloride<br>MP: | $F_2C=C(F)-(CH_2)_2-NH-C(=O)-CH_2-NH_3^+\,Cl^-$ | C 32.97<br>H 4.61<br>Cl 16.22<br>F 26.07<br>N 12.81 | 32.83<br>4.65<br><br><br>12.73 |
| 38 | pentanediamide,-2-amino-n(superscript 1)-(3,-4,-4-trifluoro-3-butenyl)-,-monohydro-chloride,-(S)-<br>MP: | $F_2C=C(F)-(CH_2)_2-NH-C(=O)-C(H)(NH_3^+Cl^-)-(CH_2)_2-C(=O)-NH_2$<br>L - ISOMER | C 37.32<br>H 5.22<br>Cl 12.24<br>F 19.68<br>N 14.51 | 37.09<br>5.16<br><br><br>14.26 |
| 39 | pentanoic acid,-4-amino-5-oxo-5-[(3,-4,-4-trifluoro-3-butenyl)-amino]-,-monohydro-chloride,-(S)-<br>MP: | $F_2C=C(F)-(CH_2)_2-NH-C(=O)-C(H)(NH_3^+Cl^-)-(CH_2)_2-C(=O)-OH$<br>L - ISOMER | C 37.19<br>H 4.85<br>Cl 12.20<br>F 19.61<br>N 9.64 | 37.15<br>4.81<br><br><br>9.66 |
| 40 | butanamide,-2-amino-4-(methylthio)-N-(3,-4,-4-trifluoro-3-butenyl)-,-monohydro-chloride,-(S)-<br>MP: 108.0–110.0 | $F_2C=C(F)-(CH_2)_2-NH-C(=O)-C(H)(NH_3^+Cl^-)-(CH_2)_2-S-CH_3$<br>L - ISOMER | C 36.92<br>H 5.51<br>Cl 12.11<br>F 19.47<br>N 9.57<br>S 10.95 | 37.01<br>5.54<br><br><br>9.53<br>11.04 |
| 41 | propanamide,-3-amino-N-(3,-4,-4-trifluoro-3-butenyl)-,-monohydrochloride<br>MP: 126.0–128.0 | $F_2C=C(F)-(CH_2)_2-NH-C(=O)-(CH_2)_2-NH_3^+\,Cl^-$ | C 36.14<br>H 5.20<br>Cl 15.24<br>F 24.50<br>N 12.04 | 36.24<br>5.20<br><br><br>12.00 |
| 42 | butanamide,-2-amino-3-methyl-N-(3,-4,-4-trifluoro-3-butenyl)-,-(S)-,-monohydrochloride<br>MP: 84.0–86.0 | $F_2C=C(F)-(CH_2)_2-NH-C(=O)-C(H)(NH_3^+Cl^-)-CH(CH_3)-CH_3$<br>L - ISOMER | C 41.47<br>H 6.19<br>Cl 13.60<br>F 21.86<br>N 10.75 | 40.07<br>6.22<br><br><br>10.33 |
| 43 | butanamide,-4-amino-N-(3,-4,-4-trifluoro-3-butenyl)-,-monohydrochloride<br>MP: 93.0–95.0 | $F_2C=C(F)-(CH_2)_2-NH-C(=O)-(CH_2)_3-NH_3^+\,Cl^-$ | C 38.95<br>H 5.72<br>Cl 14.37<br>F 23.11<br>N 11.36 | 37.51<br>5.65<br><br><br>10.72 |
| 44 | 2-butenoic acid,-3,-4,-4-trifluoro-<br>MP: | $F_2C=C(F)-CH_2-C(=O)-OH$ | C 34.30<br>H 2.16<br>F 40.69 | 34.28<br>2.33 |

-continued

| Example Compound # | Name | Structure | Analysis (%) | | |
|---|---|---|---|---|---|
| | | | | Calc'd | Found |
| 45 | 3-butenamide,- 3,-4,-4-trifluoro- MP: 93.0–95.0 | $F_2C=CF-CH_2-C(=O)-NH_2$ | C H F N | 34.54 2.90 40.98 10.07 | 35.28 2.97 9.73 |
| 46 | 3-buten-1-amine,- 4,-4-difluoro-,- monohydrochloride MP: | $F_2C=CH-(CH_2)_2-NH_3^+ Cl^-$ | C H Cl F N | 33.46 5.62 24.69 26.47 9.76 | 30.43 5.61 10.23 |
| 47 | 3-butenoic acid,- 3,-4,-4-trifluoro-,- sodium salt MP: 250.0 | $CF_2=CF-CH_2-C(=O)-O^- Na^+$ | C H F Na | 29.65 1.24 35.17 14.19 | 29.62 1.29 |
| 48 | 3-butenoic acid,- 3,-4,-4-trifluoro-,- compd. with 3,-4,-4-trifluoro-3-buten-1-amine (1:1)- MP: 67.0–69.0 | $CF_2=CF-CH_2-C(=O)-O^- NH_3^+-CH_2-CH_2-CF=CF_2$ | C H F N | 36.24 3.42 42.99 5.28 | 36.34 3.40 5.21 |
| 49 | dl-valine,- N-(3,-4,-4-trifluoro-3-butenyl)-,- methyl ester,- monohydrochloride MP: 162.0–164.0 | $F_2C=CF-(CH_2)_2-NH-CH(CH(CH_3)_2)-C(=O)-O-CH_3 \cdot HCl$ | C H Cl F N | 43.56 6.22 12.86 20.67 5.08 | 43.66 6.25 5.04 |
| 50 | acetamide,- 2,-2,-2-trifluoro-N-(3,-4,-4-trifluoro-3-butenyl)- MP: | $F_2C=CF-(CH_2)_2-NH-C(=O)-CF_3$ | C H F N | 32.59 2.28 51.56 6.33 | 32.79 2.47 6.35 |
| 51 | acetamide,- N-(3,-4,-4-trifluoro-3-butenyl)- MP: | $F_2C=CF-(CH_2)_2-NH-C(=O)-CH_3$ | C H F N | 43.12 4.82 34.10 8.38 | 42.02 4.99 8.17 |
| 52 | propanamide,- N-(3,-4,-4-trifluoro-3-butenyl)- MP: | $F_2C=CF-(CH_2)_2-NH-C(=O)-CH_2-CH_3$ | C H F N | 46.41 5.56 31.46 7.73 | 46.30 5.54 7.65 |
| 53 | propanamide,- 2,-2-dimethyl-N-(3,-4,-4-trifluoro-3-butenyl)- MP: 42.0–44.0 | $CH_3-C(CH_3)(CH_3)-C(=O)-NH-(CH_2)_2-CF=CF_2$ | C H F N | 51.67 6.75 27.24 6.69 | 51.70 6.72 6.72 |
| 54 | 2-pyrrolidine-carboxamde,- N-(3,-4,-4-trifluoro-3-butenyl)-,- (S)-,- monohydrochloride MP: | $F_2C=CF-(CH_2)_2-NH-C(=O)-[pyrrolidine \cdot H_2N^+ \cdot Cl^-]$ L-ISOMER | C H Cl F N | 41.79 5.46 13.71 22.04 10.83 | 40.62 5.33 10.39 |
| 55 | butanediamide,- 2-amino-n(superscript 1)-||(3,-4,-4-trifluoro-3-butenyl)amino|-carbonyl|-,- monohydrochloride,- (S)- MP: | $F_2C=CF-(CH_2)_2-NH-C(=O)-C(H)(CH_2-C(=O)-NH_2)-NH_3^+ Cl^-$ L-ISOMER | C H Cl F N | 34.86 4.75 12.86 20.68 15.24 | 32.55 4.90 14.54 |

-continued

| Example Compound # | Name | Structure | Analysis (%) Calc'd | Found |
|---|---|---|---|---|
| 56 | benzenepropanamide,- alpha-amino-N- (3,-4,-4-trifluoro-3- butenyl)-,- monohydro- chloride,- (S)- MP: | $F_2C=C(F)-(CH_2)_2-NH-C(=O)-\overset{CH_2-C_6H_5}{\underset{H}{C}}-NH_3^+ Cl^-$  L - ISOMER | C 50.57 H 5.22 Cl 11.48 F 18.46 N 9.07 | 49.68 5.32 8.93 |
| 57 | pentanamide,- -2-amino-4-methyl- N-(3,-4,-4-trifluoro- 3-butenyl)-,- monohydro- chloride,- (S)- MP: 114.0–116.0 | $F_2C=C(F)-(CH_2)_2-NH-C(=O)-\overset{CH_2-CH(CH_3)-CH_3}{\underset{H}{C}}-NH_3^+ Cl^-$  L - ISOMER | C 43.72 H 6.60 Cl 12.91 F 20.75 N 10.20 | 43.86 6.61 10.23 |
| 58 | pentanamide,- -2-amino-3-methyl- N-(3,-4,-4-trifluoro- 3-butenyl)-,- monohydro- chloride,- (S)- MP: | $F_2C=C(F)-(CH_2)_2-NH-\underset{O}{\overset{}{C}}(=O)-\overset{CH_3-CH(CH_3)-CH_3}{\underset{H}{C}}-NH_3^+ Cl^-$  L - ISOMER | C 43.72 H 6.60 Cl 12.91 F 20.75 N 10.20 | 42.80 6.64 10.00 |
| 59 | 7-octen-1-amine,- 7,-8,-8-trifluoro-,- monohydrochloride MP: | $F_2C=C(F)-(CH_2)_6-NH_2 \cdot HCl$ | C 44.14 H 6.95 Cl 16.29 F 26.19 N 6.44 | |
| 60 | butanamide,- 2-amino-N-(3,-4,-4- trifluoro-3- butenyl)-,- monohydro- chloride,- (S)- MP: 144.0–148.0 | $F_2C=C(F)-(CH_2)_2-NH-\underset{O}{\overset{}{C}}(=O)-\overset{CH_2-CH_3}{\underset{H}{C}}-NH_3^+ Cl^-$  L - ISOMER | C 38.95 H 5.72 Cl 14.37 F 23.11 N 11.36 | 38.75 5.78 11.36 |
| 61 | pentanamide,- 2-amino-N-(3,-4,-4- trifluoro-3- butenyl)-,- monohydro- chloride,- (S)- MP: 161.0–163.0 | $F_2C=C(F)-(CH_2)_2-NH-\underset{O}{\overset{}{C}}(=O)-\overset{(CH_2)_2-CH_3}{\underset{H}{C}}-NH_3^+ Cl^-$  L - ISOMER | C 41.47 H 6.19 Cl 13.60 F 21.86 N 10.75 | 41.55 6.16 10.68 |
| 62 | butanamide,- 2-amino-3-hydroxy- N-(3,-4,-4-trifluoro- 3-butenyl)-,- monohydro- chloride,- (S)- MP: | $F_2C=C(F)-(CH_2)_2-NH-\underset{O}{\overset{}{C}}(=O)-\overset{HO-CH-CH_3}{\underset{H}{C}}-NH_3^+ Cl^-$  L - ISOMER | C 36.58 H 5.37 Cl 13.50 F 21.70 N 10.67 | 36.41 5.42 10.57 |
| 63 | hexanamide,- 2,-6-diamino-N-(3,- 4,-4-trifluoro-3- butenyl)-,- dihydrochloride,- (S)- MP: | $F_2C=C(F)-(CH_2)_2-NH-\underset{O}{\overset{}{C}}(=O)-\overset{(CH_2)_4-NH_3^+}{\underset{H}{C}}-NH_3^+ \cdot 2Cl^-$  L - ISOMER | C 36.82 H 6.18 Cl 21.74 F 17.47 N 12.88 | 36.01 6.17 12.32 |

-continued

| Example Compound # | Name | Structure | Analysis (%) Calc'd | Found |
|---|---|---|---|---|
| 64 | L-alpha-asparagine,-N-(3,-4,-4-trifluoro-3-butenyl)-,-monohydrochloride MP: | 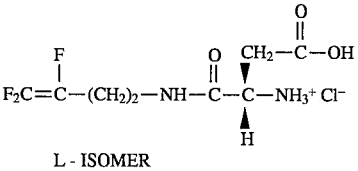<br>L - ISOMER | C 34.73<br>H 4.37<br>Cl 12.82<br>F 20.60<br>N 10.13 | 34.66<br>4.40<br><br><br>10.11 |
| 65 | propanamide,-3,-3'-dithiobis[2-amino-N-(3,-4,-4-trifluoro-3-butenyl)-,-dihydrochloride,-(S)-<br>MP: | 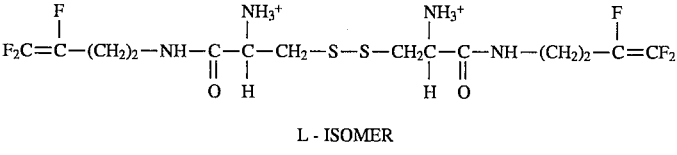<br>L - ISOMER | C 31.88<br>H 4.20<br>Cl 13.44<br>F 21.62<br>N 10.62<br>S 12.16 | 30.43<br>4.08<br><br><br>9.98<br>11.58 |
| 66 | 3-buten-1-amine,-3,-4,-4-trifluoro-N-[(2-nitrophenyl)-methylene]-<br>MP: | 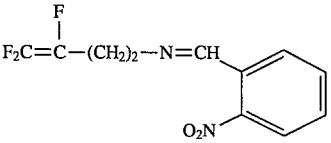 | C 51.17<br>H 3.51<br>F 22.08<br>N 10.85 | 51.45<br>3.52<br><br>10.63 |
| 67 | 2-butenoic acid,-4-oxo-4-[(3,-4,-4-trifluoro-3-butenyl)-amino]-,-(E)-<br>MP: 183.0–185.0 | 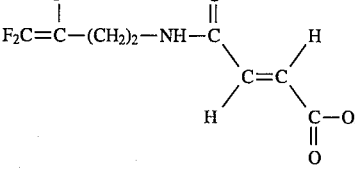 | C 43.06<br>H 3.61<br>F 25.54<br>N 6.28 | 43.20<br>3.61<br><br>6.17 |
| 68 | pentanoic acid,-5-oxo-5-[(3,-4,-4-trifluoro-3-butenyl)-amino]-<br>MP: | 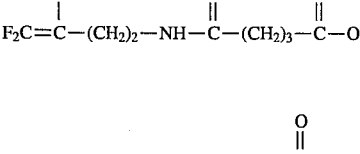 | C 45.19<br>H 5.06<br>F 23.83<br>N 5.86 | 45.26<br>5.15<br><br> |
| 69 | butanedioic acid,-2-hydroxy-3-[2-oxo-2-[-(3,-4,-4-trifluoro-3-butenyl)-amino]-ethyl]-,-compd. with 3,-4,-4-trifluoro-3-buten-1-amine (1:2)-<br>MP: 139.0–142.0 | 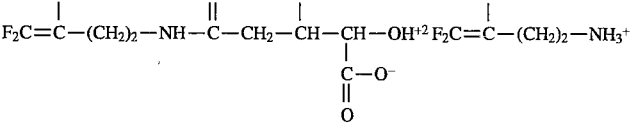 | C 39.35<br>H 4.40<br>F 31.12<br>N 7.65 | 39.26<br>4.39<br><br>7.61 |
| 70 | carbamic acid,-[3-oxo-3-[(3,-4,-4-trifluoro-3-butenyl)-amino]-propyl],-1,1'-dimethyl ethyl ester<br>MP: 78.0–80.0 | 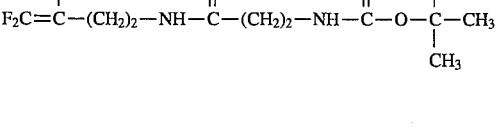 | C 48.64<br>H 6.46<br>F 19.24<br>N 9.45 | 48.82<br>6.40<br><br>9.48 |
| 71 | L-asparagine,-N-(3,-4,-4-trifluoro-3-butenyl)-,-monohydrochloride<br>MP: 152.0–154.0 | 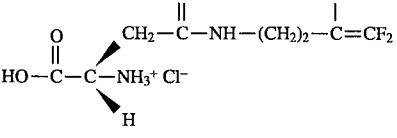<br>L - ISOMER | C 34.73<br>H 4.37<br>Cl 12.82<br>F 20.60<br>N 10.13 | 34.69<br>4.36<br><br><br>10.25 |
| 72 | 1-butene,-1,-1,-2-trifluoro-4-isocyanato-<br>MP: | 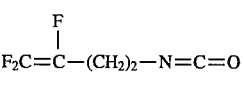 | C 39.75<br>H 2.67<br>F 37.73<br>N 9.27 | 40.74<br>2.75<br><br> |

-continued

| Example Compound # | Name | Structure | Analysis (%) Calc'd | Found |
|---|---|---|---|---|
| 73 | L-alanine,-N-ll(3,-4,-4-trifluoro-3-butenyl)-aminol-carbonyll-,-1,-1-dimethylethyl ester MP: | 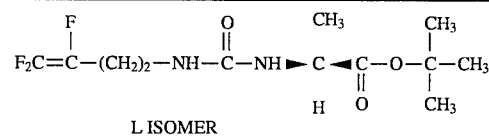 L ISOMER | C 48.64<br>H 6.46<br>F 19.24<br>N 9.45 | 48.77<br>6.48 |
| 74 | 5-hexen-1-amine,-5,-6,-6-trifluoro-,-monohydrochloride MP: | $F_2C=C(F)-(CH_2)_4-NH_2 \cdot HCl$ | C 38.01<br>H 5.85<br>Cl 18.70<br>F 30.06<br>N 7.39 | 37.74<br>5.81 |
| 75 | benzenesulfonamide,-4-methyl-N-ll(3,-4,-4-trifluoro-3-butenyl)-aminol-carbonyll-MP: 134.0–136.0 | 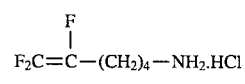 | C 44.72<br>H 4.07<br>F 17.68<br>N 8.69<br>S 9.95 | 44.78<br>4.05<br>8.66 |
| 76 | glycine,-N-(4,4-difluoro-3-butenyl)-,-methyl ester,-monohydrochloride MP: 145.0–147.0 | $F_2C=CH-(CH_2)_2-NH-CH_2-C(=O)-O-CH_3 \cdot HCl$ | C 38.99<br>H 5.61<br>Cl 16.44<br>F 17.62<br>N 6.50 | 38.80<br>5.67<br>6.66 |
| 77 | urea,-N-l2-hydroxy-1-(hydroxymethyl)-ethyll-n'-(3,-4,-4-trifluoro-3-butenyl)-MP: 115.0–118.0 | 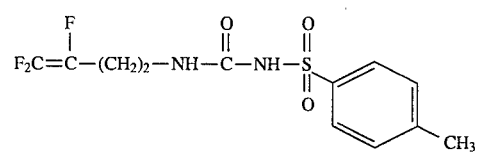 | C 39.67<br>H 5.41<br>F 23.53<br>N 11.57 | 39.78<br>5.41<br>11.62 |
| 78 | urea,-N-hydroxy-n'-(3,-4,-4-trifluoro-3-butenyl)-MP: 112.0–115.0 | $F_2C=C(F)-(CH_2)_2-NH-C(=O)-NH-OH$ | C 32.62<br>H 3.83<br>F 30.96<br>N 15.21 | 32.72<br>3.74<br>15.11 |
| 79 | propanamide,-2-amino-N-(3,-4,-4-trifluoro-3-butenyl)-,-monohydrochloride,-(R)-MP: 167.0 | 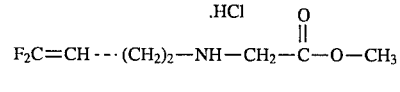 D - ISOMER | C 36.14<br>H 5.20<br>Cl 15.24<br>F 24.50<br>N 12.04 | 36.30<br>5.24<br>11.97 |
| 80 | 3-buten-1-amine,-3,-4,-4-trifluoro-,-ethanedioate (2:1)-MP: 179.0–181.0 | 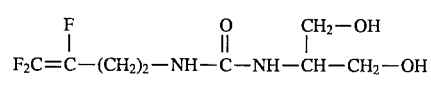 | C 35.30<br>H 4.15<br>F 33.51<br>N 8.23 | 35.37<br>4.16<br>8.40 |
| 81 | benzenepropanamide,-alpha-amino-4-hydroxy-N-(3,-4,-4-trifluoro-3-butenyl)-,-monohydrochloride,-(S)-MP: | 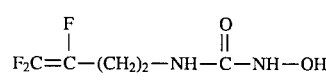 (L) | C 48.08<br>H 4.97<br>Cl 10.92<br>F 17.55<br>N 8.63 | 46.62<br>4.98<br>9.31 |
| 82 | 2-butenoic acid,-3,-4,-4-trifluoro-,-compd. with 2-propanamine (1:1)-MP: 86.0–88.0 | 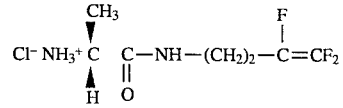 | C 42.21<br>H 6.07<br>F 28.62<br>N 7.03 | 42.30<br>6.05<br>7.07 |

-continued

| Example Compound # | Name | Structure | Analysis (%) Calc'd | Found |
|---|---|---|---|---|
| 83 | 2-butenoic acid,-3,-4,-4-trifluoro-,-ammonium salt MP: 127.0–129.0 | $F_2C=CF-CH_2-\overset{O}{\underset{\|}{C}}-O^-\ NH_4^+$ | C 30.58<br>H 3.85<br>F 36.28<br>N 8.92 | 30.82<br>3.87<br><br>8.88 |
| 84 | 7-octenoic acid,-7,-8,-8-trifluoro-MP: | $\underset{F}{\overset{F\ \ F}{\underset{\|}{C}=\underset{\|}{C}}}-CH_2-CH_2-CH_2-CH_2-CH_2-\overset{O}{\underset{\|}{C}}-OH$ | C 48.98<br>H 5.65<br>F 29.06 | 49.09<br>5.65 |
| 85 | 11-dodecenoic acid,-11,-12,-12-trifluoro-MP: | $\underset{F}{\overset{F\ \ F}{\underset{\|}{C}=\underset{\|}{C}}}-(CH_2)_9-\overset{O}{\underset{\|}{C}}-OH$ ..1 $CH_3-(CH_2)_6-\overset{O}{\underset{\|}{C}}-OH$ | C 57.64<br>H 7.79<br>F 21.37 | 57.72<br>7.75 |
| 86 | butanoic acid,-4-oxo-4-[(5,-6,-6-trifluoro-5-hexenyl)-amino]-MP: 50.0–60.0 | $\underset{F}{\overset{F\ \ F}{\underset{\|}{C}=\underset{\|}{C}}}-CH_2-CH_2-CH_2-CH_2-\overset{H}{N}-\overset{O}{\underset{\|}{C}}-CH_2-CH_2-\overset{O}{\underset{\|}{C}}-OH$ | C 47.43<br>H 5.57<br>F 22.51<br>N 5.53 | 47.47<br>5.57 |
| 87 | butanoic acid,-4-oxo-4-[(7,-8,-8-trifluoro-7-octenyl)-amino]-MP: 61.0–63.0 | $\underset{F}{\overset{F\ \ F}{\underset{\|}{C}=\underset{\|}{C}}}-CH_2-CH_2-CH_2-CH_2-CH_2-CH_2-\overset{H}{N}-\overset{O}{\underset{\|}{C}}-CH_2-CH_2-\overset{O}{\underset{\|}{C}}-OH$ | C 51.24<br>H 6.45<br>F 20.26<br>N 4.98 | 51.28<br>6.47 |
| 88 | benzoic acid,-2-[(3,-4,-4-trifluoro-3-butenyl)-amino]-MP: 89.0–95.0 | F₂C=CF–CH₂–CH₂–NH–(2-carboxyphenyl) | C 53.88<br>H 4.11<br>F 23.25<br>N 5.71 | 54.00<br>4.15 |
| 89 | 3-butenamide,-N,-N-diethyl-3,-4,-4-trifluoro-MP: | F₂C=CF–CH₂–C(=O)–N(CH₂CH₃)₂ | C 49.23<br>H 6.20<br>F 29.20<br>N 7.18 | 49.27<br>6.15 |
| 90 | glycine,-N-(3,-4,-4-trifluoro-1-oxo-3-butenyl)-,-1,-1-dimethylethyl ester MP: 52.0–54.0 | $F-\underset{\underset{F}{\|}}{\overset{}{C}}=\underset{\underset{F}{\|}}{\overset{}{C}}-CH_2-\overset{O}{\underset{\|}{C}}-\overset{H}{N}-CH_2-\overset{O}{\underset{\|}{C}}-O-\overset{CH_3}{\underset{CH_3}{\overset{\|}{\underset{\|}{C}}}}-CH_3$ | C 47.43<br>H 5.57<br>F 22.51<br>N 5.53 | |
| 91 | glycine,-N-(3,-4,-4-trifluoro-1-oxo-3-butenyl)-MP: 115.0–116.0 | $F-\underset{\underset{F}{\|}}{\overset{}{C}}=\underset{\underset{F}{\|}}{\overset{}{C}}-CH_2-\overset{O}{\underset{\|}{C}}-\overset{H}{N}-CH_2-\overset{O}{\underset{\|}{C}}-O-H$ | C 36.56<br>H 3.07<br>F 28.92<br>N 7.11 | 36.65<br>3.06<br><br>7.10 |
| 92 | L-phenylalanine,-N-(3,-4,-4-trifluoro-1-oxo-3-butenyl)-,-1,-1-dimethylethyl ester MP: 59.0–62.0 | $\underset{F}{\overset{F}{\underset{\diagdown}{}}}C=\underset{\underset{F}{\|}}{\overset{}{C}}-CH_2-\overset{O}{\underset{\|}{C}}-\overset{H}{N}-\overset{\underset{CH_2-Ph}{\|}}{CH}-\overset{O}{\underset{\|}{C}}-O-\overset{CH_3}{\underset{CH_3}{\overset{\|}{\underset{\|}{C}}}}-CH_3$ | C 59.47<br>H 5.87<br>F 16.60<br>N 4.08 | 59.47<br>5.84<br><br>4.09 |

-continued

| Ex-ample Compound # | Name | Structure | Analysis (%) | |
|---|---|---|---|---|
| | | | Calc'd | Found |
| 93 | L-asparagine,-N-(3,-4,-4-trifluoro-1-oxo-3-butenyl)-,-1,-1-dimethylethyl ester MP: 121.0–124.0 | 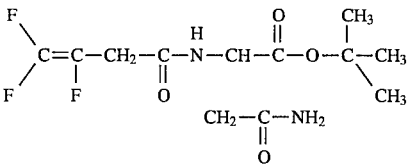 | C 46.45<br>H 5.52<br>F 18.37<br>N 9.03 | 46.43<br>5.57<br><br>9.04 |
| 94 | L-phenylalanine,-N-(3,-4,-4-trifluoro-1-oxo-3-butenyl)-MP: 134.0–135.5 | 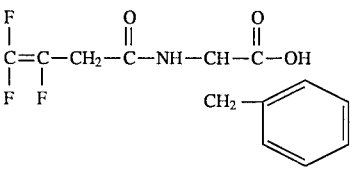 | C 54.36<br>H 4.21<br>F 19.84<br>N 4.88 | 54.28<br>4.22<br><br>4.85 |
| 95 | L-asparagine,-N-(3,-4,-4-trifluoro-1-oxo-3-butenyl)-MP: 146.0–149.0 | 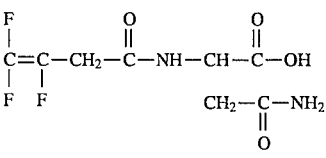 | C 37.80<br>H 3.57<br>F 22.43<br>N 11.02 | 37.86<br>3.59<br><br>11.04 |
| 96 | 3-butenamide,-N-(2-aminoethyl)-3,-4,-4-trifluoro-,-monohydrochloride MP: 145.0–147.0 | 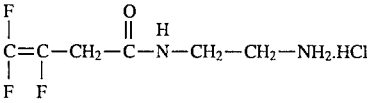 | C 32.97<br>H 4.61<br>Cl 16.22<br>F 26.07<br>N 12.81 | |
| 97 | carbamic acid,-[3-[(3,-4,-4-trifluoro-1-oxo-3-butenyl)-amino]-propyl]-,-1,-1-dimethylethyl ester MP: 82.5–83.6 | 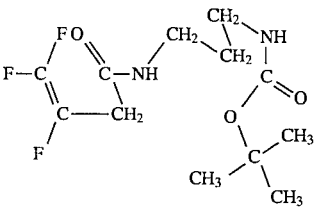 | C 48.64<br>H 6.46<br>F 19.24<br>N 9.45 | 48.71<br>6.43<br><br>9.44 |
| 98 | 3-butenamide,-N-(3-aminopropyl)-3,-4,-4-trifluoro-,-monohydrochloride MP: 132.0–133.5 | 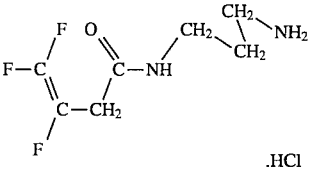 | C 36.14<br>H 5.20<br>Cl 15.24<br>F 24.50<br>N 12.04 | 36.04<br>5.25<br><br><br>11.97 |
| 99 | piperazine,-1,-4-bis(3,-4,-4-trifluoro-1-oxo-3-butenyl)-MP: 132.5–134.0 | 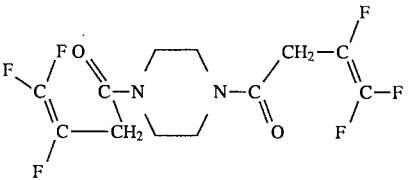 | C 43.64<br>H 3.66<br>F 31.52<br>N 8.18 | 43.75<br>3.67<br><br>8.51 |
| 100 | 3-butenamide, N-(4-aminobutyl)-3,4,4-trifluoro-, monohydrochloride MP: 143.0–144.0 | 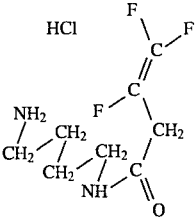 | C 38.95<br>H 5.72<br>Cl 14.37<br>F 23.11<br>N 11.36 | 39.05<br>5.73<br><br><br>11.28 |

-continued

| Example Compound # | Name | Structure | Analysis (%) Calc'd | Found |
|---|---|---|---|---|
| 101 | 3-butenoyl chloride, 3,4,4-trifluoro- MP: | 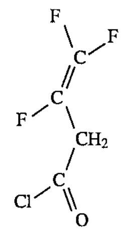 | C 30.31<br>H 1.27<br>Cl 22.37<br>F 35.96 | 29.76<br>1.27 |
| 102 | morpholine,-4-(3,-4,-4-trifluoro-1-oxo-3-butenyl)- MP: 80.0–81.0 | 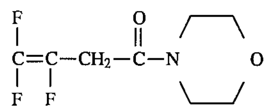 | C 45.94<br>H 4.82<br>F 27.25<br>N 6.70 | |
| 103 | 3-butenamide,-N-butyl-3,-4,-4-trifluoro- MP: 34.0–36.0 | 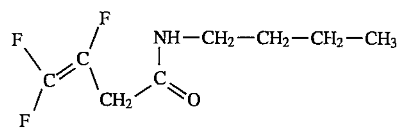 | C 49.23<br>H 6.20<br>F 29.20<br>N 7.18 | 49.33<br>6.22 |
| 104 | 5-hexenoic acid,-5,-6,-6-trifluoro- MP: | 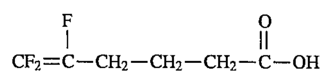 | C 42.87<br>H 4.20<br>F 33.90 | 42.83<br>4.17 |
| 105 | 3-butenamide,-3,-4,-4-trifluoro-N-hydroxy- MP: 99.0–100.0 | 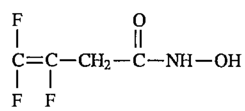 | C 30.98<br>H 2.60<br>F 36.75<br>N 9.03 | 31.54<br>2.63<br>9.20 |
| 106 | 3-butenoic acid,-3,-4,-4-trifluoro-,-(2,-2-dimethyl-1,-3-dioxolan-4-yl)-methyl ester MP: | 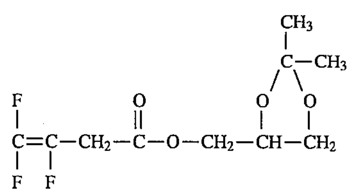 | C 47.25<br>H 5.15<br>F 22.42 | 48.28<br>5.40 |
| 107 | benzoic acid,-4-[(3,-4,-4-trifluoro-3-butenyl)-amino]-,-methyl ester MP: 47.0–49.0 | 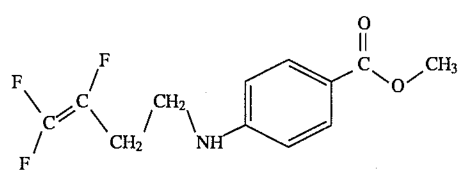 | C 55.60<br>H 4.67<br>F 21.99<br>N 5.40 | 55.58<br>4.68<br>5.37 |
| 108 | acetamide,-2-[(3,-4,-4-trifluoro-3-butenyl)-amino]-,-monohydrochloride MP: 198.0–200.0 | 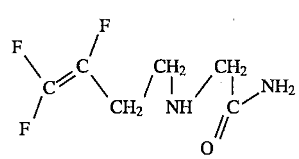 | C 32.97<br>H 4.61<br>Cl 16.22<br>F 26.07<br>N 12.81 | 33.08<br>4.57<br>12.80 |
| 109 | benzoic acid,-4-[(3,-4,-4-trifluoro-3-butenyl)-amino]- MP: 149.0–151.0 | 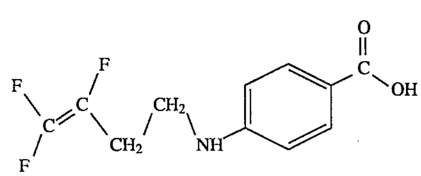 | C 53.88<br>H 4.11<br>F 23.25<br>N 5.71 | 53.82<br>4.13<br>5.69 |

-continued

| Example Compound # | Name | Structure | Analysis (%) | | |
|---|---|---|---|---|---|
| | | | | Calc'd | Found |
| 110 | 3-buten-1-amine,-3,-4,-4-trifluoro-N-(phenylmethylene)-MP: | 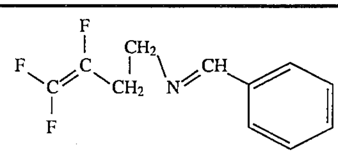 | C<br>H<br>F<br>N | 61.97<br>4.73<br>26.73<br>6.57 | 61.92<br>4.68<br><br>6.56 |
| 111 | benzoic acid,-3-[(3,-4,-4-trifluoro-3-butenyl)-amino]-,-methyl ester MP: | 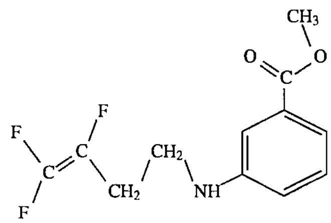 | C<br>H<br>F<br>N | 55.60<br>4.67<br>21.99<br>5.40 | 55.58<br>4.55<br><br>5.45 |
| 112 | benzoic acid,-3-[(3,-4,-4-trifluoro-3-butenyl)-amino]-,-monohydrochloride MP: 222.0–224.0 | 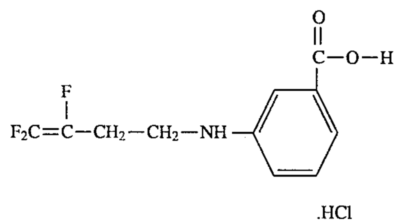 | C<br>H<br>Cl<br>F<br>N | 46.91<br>3.94<br>12.59<br>20.24<br>4.97 | 46.92<br>3.94<br><br><br>4.96 |
| 113 | 3-butanoic acid,-3,-4,-4-trifluoro-,-phenylmethylester MP: | 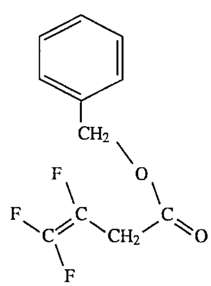 | C<br>H<br>F | 57.40<br>3.94<br>24.76 | 57.38<br>3.92<br>  |
| 114 | 3-butenoic acid,-3,-4,-4-trifluoro-,-octylester MP: | 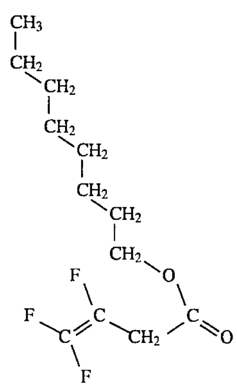 | C<br>H<br>F | 57.13<br>7.59<br>22.59 | 57.12<br>7.54<br>  |

-continued

| Example Compound # | Name | Structure | Analysis (%) Calc'd | Found |
|---|---|---|---|---|
| 115 | 3-butenamide,-3,-4,-4-trifluoro-N-phenyl- MP: 118.0–122.0 | 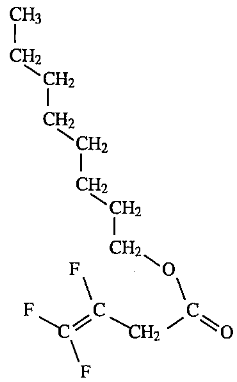 | C 55.82<br>H 3.75<br>F 26.49<br>N 6.51 | 55.86<br>3.73 |
| 116 | 3-butenoic acid,-3,-4,-4-trifluoro-,-phenylester MP: | 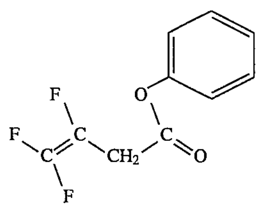 | C 55.56<br>H 3.26<br>F 26.37 | 55.30<br>3.25 |
| 117 | 3-butenoic acid,-3,-4,-4-trifluoro-,-4-nitrophenyl ester MP: 58.0–62.0 | 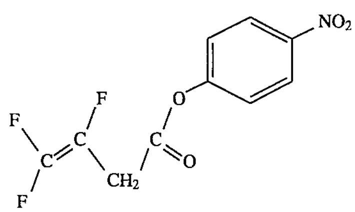 | C 45.99<br>H 2.32<br>F 21.83<br>N 5.36 | 45.74<br>2.25 |
| 118 | 3-butenoic acid,-3,-4,-4-trifluoro-,-3-methylbutyl ester MP: | 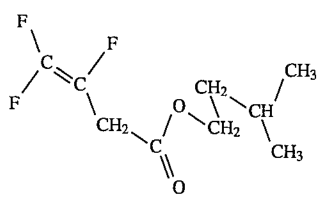 | C 51.43<br>H 6.23<br>F 27.12 | 51.44<br>6.20 |
| 119 | 3-butenethioic acid,-3,-4,-4-trifluoro-,-S-phenyl ester MP: | 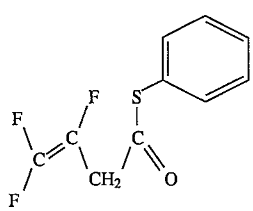 | C 51.72<br>H 3.04<br>F 24.54<br>S 13.81 | 51.98<br>3.09 |
| 120 | 3-butenoic acid,-3,-4,-4-trifluoro-,-2-(3,-4,-4-trifluoro-1-oxo-3-butenyl)-hydrazide MP: 191.0–193.0 | 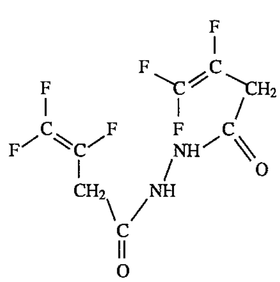 | C 34.80<br>H 2.19<br>F 41.28<br>N 10.14 | 34.89<br>2.23 |

-continued

| Example Compound # | Name | Structure | Analysis (%) | Calc'd | Found |
|---|---|---|---|---|---|
| 121 | 3-butenethioic acid,-3,-4,-4-trifluoro-,-S-octyl ester MP: | 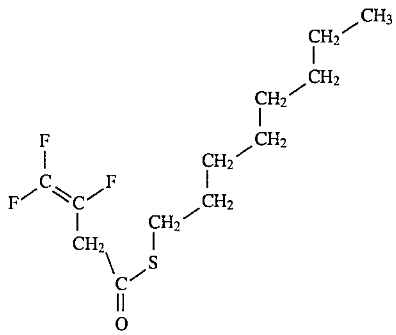 | C<br>H<br>F<br>S | 53.71<br>7.14<br>21.24<br>11.95 | 53.82<br>7.13 |
| 122 | 3-butenethioic acid,-3,-4,-4-trifluoro-,-S-(phenylmethyl)-ester MP: | 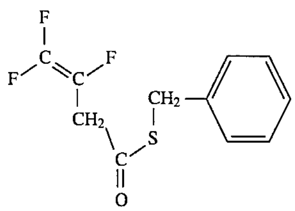 | C<br>H<br>F<br>S | 53.65<br>3.68<br>23.15<br>13.02 | 53.67<br>3.68 |
| 123 | L-alanine,-N-(3,-4,-4-trifluoro-1-oxo-3-butenyl)-MP: 98.0–103.0 | (L—) | C<br>H<br>F<br>N | 39.82<br>3.82<br>27.00<br>6.63 | 39.83<br>3.80 |
| 124 | L-valine,-N-(3,-4,-4-trifluoro-1-oxo-3-butenyl)-MP: 145.0–150.0 | (L—) | C<br>H<br>F<br>N | 45.19<br>5.06<br>23.83<br>5.86 | 45.26<br>5.09 |
| 125 | L-proline,-1-(3,-4,-4-trifluoro-1-oxo-3-butenyl)-MP: | (L—) +0.2 OF3OOOH | C<br>H<br>F<br>N | 45.58<br>4.25<br>24.03<br>5.91 | 43.34<br>4.18 |

-continued

| Ex-ample Compound # | Name | Structure | Analysis (%) | |
|---|---|---|---|---|
| | | | Calc'd | Found |
| 126 | L-aspartic acid,-N-(3,-4,-4-trifluoro-1-oxo-3-butenyl)-MP: | (L—) +0.2 C2H5OC2H5 | C 37.66<br>H 3.16<br>F 22.34<br>N 5.49 | 38.99<br>3.74 |
| 127 | 3-butenethioic acid,-3,-4,-4-trifluoro,-S-(2-aminoethyl)-ester<br>MP: 95.0–115.0 | 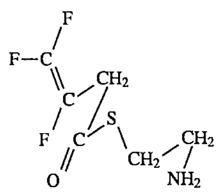 | C 26.48<br>H 3.70<br>Cl 26.06<br>F 20.95<br>N 5.15<br>S 11.78 | 30.87<br>3.87 |
| 128 | benzoic acid,-3-[(3,-4,-4-trifluoro-1-oxo-3-butenyl)-amino]-<br>MP: 252.0–255.0 | 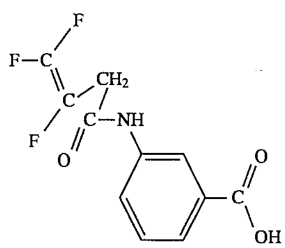 | C 50.97<br>H 3.11<br>F 21.99<br>N 5.40 | 50.96<br>3.13 |
| 129 | benzoic acid,-2-[(3,-4,-4-trifluoro-1-oxo-3-butenyl)-thiol-<br>MP: 48.0–58.0 | +0.4 CH3OH | C 17.83<br>H 2.55<br>F 20.63<br>S 11.61 | 48.35<br>2.82 |
| 130 | 3-butenoic acid,-3,-4,-4-trifluoro-,-2-aminoethyl ester,-monohydrochloride<br>MP: 94.0–100.0 | HCl | C 28.14<br>H 3.94<br>Cl 27.69<br>F 22.26<br>N 5.47 | 32.53<br>4.19 |
| 131 | 3H-pyrazol-3-one,-2,-4-dihydro-4-[[(3,-4,-4-trifluoro-3-butenyl)-amino]-methylene]-<br>MP: 126.0–130.0 | 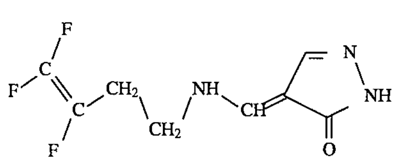 | C 43.84<br>H 3.68<br>F 26.01<br>N 19.17 | 43.88<br>3.69 |

-continued

| Example Compound # | Name | Structure | Analysis (%) Calc'd | Found |
|---|---|---|---|---|
| 132 | benzenamine,- N-(3,-4,-4-trifluoro- 3-butenyl)- MP: | 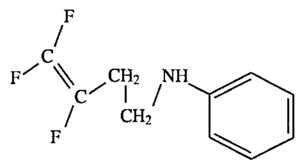 | C 59.70<br>H 5.01<br>F 28.33<br>N 6.96 | 5.01<br>5.05 |
| 133 | carbamic acid,- -[3-[(3,-4,-4- trifluoro-3-butenyl)- amino]-propyl],-1,-1- dimethylethyl ester MP: | 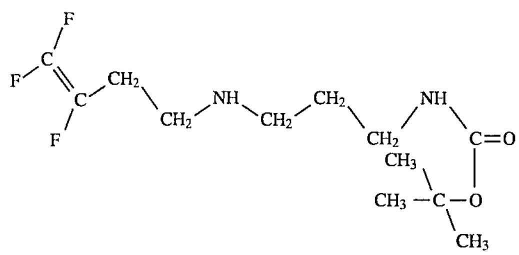 | C 51.05<br>H 7.50<br>F 20.19<br>N 9.92 | 51.07<br>7.54 |
| 134 | 1,-3-propane- diamine,-N- (3,-4,-4-trifluoro-3- butenyl)-,- dihydrochloride MP: 225.0–270.0 | 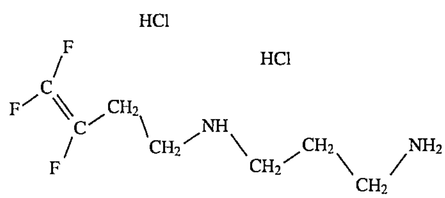 | C 28.84<br>H 5.53<br>Cl 36.48<br>F 19.55<br>N 9.61 | 33.02<br>5.95 |
| 135 | 2-thiophene- carboxylic acid,- 3-[(3,-4,-4-trifluoro- 3-butenyl)-amino]-,- methyl ester MP: | 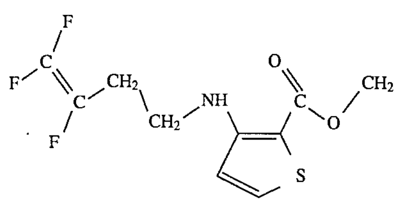 | C 45.28<br>H 3.80<br>F 21.49<br>N 5.28<br>F 12.09 | 45.28<br>3.77 |
| 136 | 1,-2-ethanediamine,- N-(3,-4,-4-trifluoro- 3-butenyl)-,- dihydrochloride MP: 218.0–222.0 | 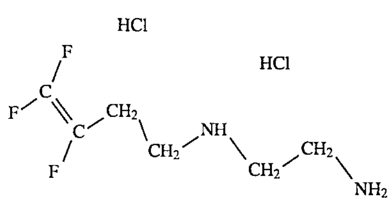 | C 25.96<br>H 5.08<br>Cl 38.32<br>F 20.54<br>N 10.09 | 29.89<br>5.45 |
| 137 | L-lysine,-n2-(3,-4,-4- trifluoro-1-oxo-3- butenyl)-,- monohydrochloride MP: 54.0 | (L—)<br>+0.5 ET20 + 0.6 H20 | C 35.21<br>H 5.02<br>Cl 20.78<br>F 16.71<br>N 8.21 | 40.69<br>6.49 |

-continued

| Ex-ample Compound # | Name | Structure | Analysis (%) | | |
|---|---|---|---|---|---|
| | | | | Calc'd | Found |
| 138 | cyclopropane-carboxamide,-1-amino-N-(3,-4,-4-trifluoro-3-butenyl)-,-monohydrochloride MP: 55.0–70.0 | 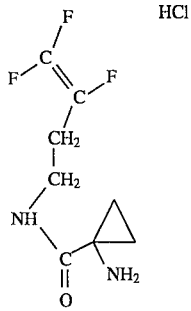 +0.3 H2O | C<br>H<br>Cl<br>F<br>N | 39.28<br>4.94<br>14.49<br>23.30<br>11.45 | 38.34<br>4.98 |
| 139 | butanoic acid,-4-[(4,-4-difluoro-3-butenyl)-amino]-4-oxo- MP: 50.0–53.0 | 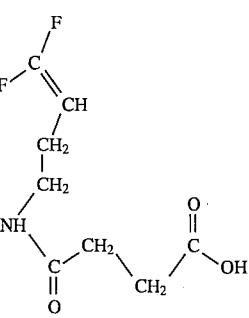 | C<br>H<br>F<br>N | 46.38<br>5.35<br>18.34<br>6.76 | 46.17<br>5.37 |
| 140 | propanamide,-2-amino-N-(4,-4-difluoro-3-butenyl)-,-monohydro-chloride,-(S)- MP: | 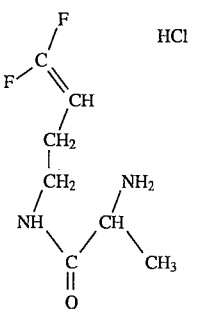 L-Form (+0.4 H2O) | C<br>H<br>Cl<br>F<br>N | 39.17<br>6.10<br>16.52<br>17.70<br>13.05 | 37.87<br>6.24 |
| 141 | butanamide,-2-amino-N-(4,-4-difluoro-3-butenyl)-4-(methylthio)-,-monohydro-chloride,-(S)- MP: 97.0–101.0 | 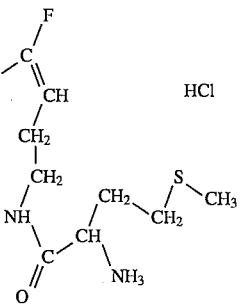 L-form | C<br>H<br>Cl<br>F<br>N<br>S | 39.34<br>6.24<br>12.90<br>13.83<br>10.20<br>11.67 | 39.57<br>6.34 |

-continued

| Example Compound # | Name | Structure | Analysis (%) Calc'd | Found |
|---|---|---|---|---|
| 142 | acetic acid,-oxo[(3,-4,-4-trifluoro-3-butenyl)-amino]-,-methyl ester<br>MP: 33.0–34.0 | 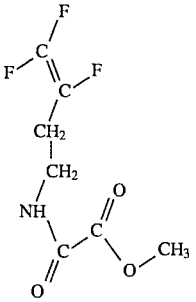 | C 39.82<br>H 3.82<br>F 27.00<br>N 6.63 | 39.92<br>3.85 |
| 143 | ethanediamide,-N-(3,-4,-4-trifluoro-3-butenyl)-<br>MP: 190.0–220.0 | 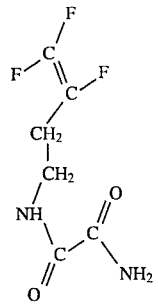<br>+0.2 H2O | C 36.74<br>H 3.60<br>F 29.06<br>N 14.28 | 36.09<br>3.68 |
| 144 | acetic acid,-[(3,-4,-4-trifluoro-3-butenyl)-amino]-oxo-,-hydrazide<br>MP: 145.0–200.0 | 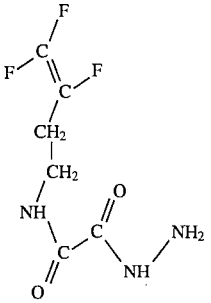<br>+0.6 H2O | C 34.13<br>H 3.82<br>F 27.00<br>N 19.90 | 32.29<br>3.99 |
| 145 | acetic acid,-[(3,-4,-4-trifluoro-3-butenyl)-amino]-oxo-<br>MP: 95.0–100.0 | 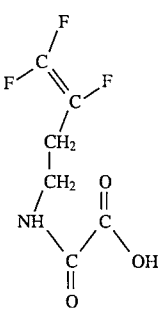 | C 36.56<br>H 3.07<br>F 28.92<br>N 7.11 | 36.77<br>3.11 |

-continued

| Example Compound # | Name | Structure | Analysis (%) Calc'd | Found |
|---|---|---|---|---|
| 146 | carbamic acid,-[1-[(1,-1-dimethyl-ethoxy)-methyl[-2-oxo-2-](3,-4,-4-trifluoro-3-butenyl)-amino]-ethyl]-,-phenylmethyl ester,-(S)-<br>MP: 68.0–72.0 | 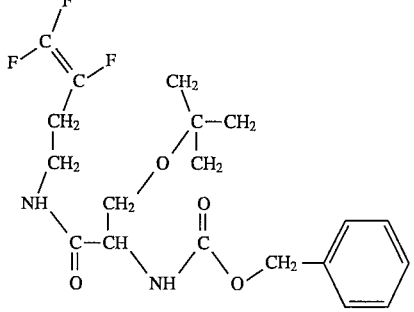<br>L - Form | C 56.71<br>H 6.26<br>F 14.16<br>N 6.96 | 56.75<br>6.26 |
| 147 | 3H-pyrazol-3-one,-4-[[4,-4-difluoro-3-butenyl)-amino]-methylene]-2,-4-dihydro-<br>MP: 120.0–124.0 | 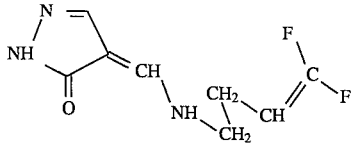 | C 47.76<br>H 4.51<br>F 18.89<br>N 20.89 | 47.02<br>4.49 |
| 148 | 3-butenamide,-3,-4,-4-trifluoro-N-(3,-4,-4-trifluoro-3-butenyl)-<br>MP: | 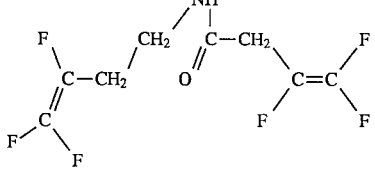 | C 38.88<br>H 2.85<br>F 46.13<br>N 5.67 | 38.51<br>2.85 |
| 149 | 3-buten-1-amine,-3,-4,-4-trifluoro-N-(3,-4,-4-trifluoro-3-butenyl)-,-monohydrochloride<br>MP: 200.0–205.0 | 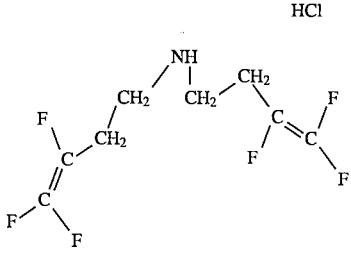 | C 35.64<br>H 3.74<br>Cl 13.15<br>F 42.28<br>N 5.19 | 35.72<br>3.73 |
| 150 | urea,-N,-N-dimethyl-n'-(3,-4,-4-trifluoro-3-butenyl)-<br>MP: 50.0–55.0 | 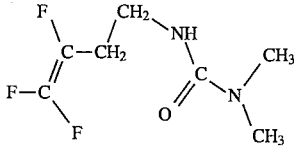 | C 42.86<br>H 5.65<br>F 29.06<br>N 14.28 | 42.79<br>5.64 |
| 151 | carbamic acid,-[1-[[(4,-4-difluoro-3-butenyl)-amino]-carbonyl]-3-(methylthio)-propyl]-,-1,-1-dimethylethyl ester,-(S)-<br>MP: 58.0–60.0 | 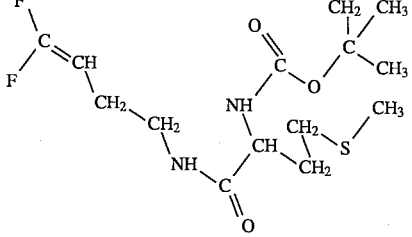<br>(L) +0.1 C4H10O | C 49.69<br>H 7.15<br>F 11.23<br>N 8.28<br>S 9.47 | 50.15<br>7.32 |

COMPOSITIONS

In normal use, the compounds usually will not be employed free from admixture or dilution, but ordinarily will be used in a suitable formulated composition compatible with the method of application and comprising an effective amount of the compound. The compounds of this invention, like most agricultural agents, may be blended with agriculturally acceptable surface-active agents and carriers normally employed for facilitating the dispersion of active ingredients, recognizing the accepted fact that the formulation and mode of application may affect the activity of the material. The present compounds may be applied, for example, as sprays, dusts, or granules, to the area where pest control is desired, the type of application varying with the pest and the environment. Thus, the compounds of this invention may be formulated as granules of large particle size, as powdery dusts, as wettable powders, as emulsifiable concentrates, as solution, and the like.

Granules may comprise porous or nonporous particles, such as attapulgite clay or sand, for example, which serve as carriers for the present compounds. The granule particles are relatively large, a diameter of about 400–2500 microns typically. The particles are either impregnated with the compound of the invention from solution or coated with the compound, adhesive sometimes being employed. Granules generally contain 0.05–10%, preferably 0.5–5%, active ingredient.

Dusts are admixtures of the compounds, with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the compound. These finely divided solids have an average particle size of less than about 50 microns. A typical dust formulation contains 1 part of compound and 99 parts of talc.

The compounds of the present invention may be made into liquid concentrates by dissolution or emulsification in suitable liquids and into solid concentrates by admixture with talc, clays, and other known solid carriers used in the agricultural chemical art. The concentrates are compositions containing about 5–50% active compound and 95–50% inert material, which includes surface-active dispersing, emulsifying, and wetting agents, but even higher concentrations of active ingredient may be employed experimentally. The concentrates are diluted with water or other liquids for practical application as sprays, or with additional solid carrier for use as dusts.

A typical 50% wettable powder formulation would consist of 50.0% (wt/wt) of active ingredient, 22.0% attapulgite diluent, 22.0% of kaolin diluent, and 6.0% sodium salts of sulfonated Kraft lignin emulsifier.

Typical carriers for solid concentrates (also called wettable powders) include fuller's earth, clays, silicas, and other highly absorbent, readily wetted inorganic diluents. A suitable solid concentrate formulation may contain 1.5 parts each of sodium lignosulfonate and sodium lauryl sulfate as wetting agents, 25 parts of active compound and 72 parts of attapulgite clay.

Manufacturing concentrates are useful for shipping low melting products of this invention. Such concentrates are prepared by melting the low melting solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the active compound with a liquid or solid emulsifying agent, or they may also contain a liquid carrier such as xylene, heavy aromatic naphthas, isophorone and other relatively non-volatile organic solvents. For application, these concentrates are dispersed in water or other liquid carriers and normally applied as sprays to areas to be treated.

A typical 50 gram per liter emulsifiable concentrate formulation would consist of 5.9% (wt/wt) of a compound of the invention; as emulsifiers; 1.80% of a blend of the calcium salt of dodecylbenzene sulfonate and nonionic 6-molar ethylene oxide condensation product of nonylphenol, 2.70% of a blend of the calcium salt of dodecylbenzene sulfonate and a nonionic 30-molar ethylene oxide condensation product of nonylphenol, 1.50% of a nonionic paste of polyalkylene glycol ether, and 88.10% refined xylene solvent.

Typical surface-active wetting, dispersing, and emulsifying agents used in agricultural formulations include, for example, the alkyl and alkylaryl sulfonates and sulfates and their sodium salts; alkylamide sulfonates, including fatty methyl taurides; alkylaryl polyether alcohols, sulfated higher alcohols, polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. The surface active agent normally comprises about 1–15% by weight of the active ingredient.

Other useful formulations include simple solutions of the active ingredient in a solvent in which it is completely soluble at the desired concentration, such as water, acetone, or other organic solvents. The preferred formulation for foliar application is an aqueous solution, more preferably containing glycerin and a surfactant, such as Tween®20, and most preferably 1% glycerin and 0.1% Tween®20.

The compositions may be formulated and applied with suitable pesticidal active ingredients, including insecticides, acaricides, fungicides, plant regulators, herbicides, fertilizers, etc.

METHODS OF USE

The present invention provides methods of controlling various pests that prey on agricultural crops, namely nematodes, insects, and acarids. An infestation of a plant by any of these pests may be controlled by applying to the plant locus an effective amount of any of the compounds of the present invention. The application may be made in a variety of ways, including applying the compound or a composition containing it to the soil before or after planting or emergence, to the seed or seed pieces prior to or at planting, and to the plant foliage, stems, or trunks. The treatment may be made more than once during a growing season with one or more days between treatments. An appropriate treatment schedule will depend on the life cycle of the pest to be controlled, ambient temperatures, and moisture levels. In addition the age or size of the plant may influence the treatment schedule.

The methods of the present invention may be carried out on a variety of crops. These include, but are not limited to, fruit and vegetable crops, such as potatoes, sweet potatoes, carrots, tomatoes, grapes, peaches, citrus, bananas, corn, and soybeans; tobacco; and cotton.

Compounds of the present invention may be used to control any of the phytopathogenic nematodes. Insects which may be controlled by the methods of the present invention include, but are not limited to, foliar pests such as green peach aphids, and soil-borne pests such as southern corn rootworm. Acarids which may be controlled by the methods of the present invention include, but are not limited to two spotted spider mites. Tests conducted with a few of the compounds of the present invention revealed no significant level of control of tobacco budworm or Colorado potato beetle.

TEST EXAMPLES

A. Tomato and soybean nematode tests

Compounds of the present invention, prepared as described above, were tested for effectiveness in controlling root knot nematode (*Meloidogyne incognita*). The compounds were tested by foliar application and by soil-drench application. The results of four different methods of testing are shown in the Table A. The methods were as follows:

Method 1. Foliar application to tomato plants

Tomato plants, cv 'Rutgers', were grown one plant per pot in 2.5×18.8 cm pots. Nineteen days after planting, both sides of the leaves were sprayed with the test compound at the concentrations indicated in Table A. The test compounds were prepared by first dissolving each in water or acetone, as appropriate, and mixing with water containing 0.05% Tween®20 and 1.0% glycerin. For each treatment rate, four plants were sprayed with 29 mL of solution. The plants were allowed to dry before transferring to growth chambers maintained at 25°–28° C. There they were sub-irrigated to prevent the leaves from dripping onto the soil. Two to three days after chemical applications, a suspension of J2 larvae, 4500 per pot, was pipetted onto the roots and soil. Three weeks after inoculation, the amount of galling on washed roots was compared to the water-treated controls. The results are reported as percent disease control.

Method 2. Foliar application to tomato plants

The Method 1 steps were followed except that (1) the tomato plants were grown in 7.5×6.3 cm² pots and (2) inoculation was made by pipetting approximately 8000 eggs in 5 mL onto the soil of each pot at 20 days after planting. The next day each plant was sprayed with 4 mL of treatment solution. The extent of galling was determined at three weeks after inoculation. A rating scale of 0 to 3 was used, 0 being extensive galling and 3 being no galling.

Method 3. Soil application to soybean seeds

Two soybean seeds, cv 'Williams,' were placed in each 2.5 cm² pot and inoculated with approximately 8000 eggs. Test compounds were added at 1 mg per pot, in 2 mL of solution prepared as described in Method 1, One pot per treatment level was used. The seeds were covered with vermiculite and lightly watered. The plants were subirrigated once a day for four weeks. The washed roots of the plants were then evaluated as in Method 2.

Method 4. Soil application to tomato plants

The Method 2 steps were followed except that the day after inoculation, treatments were applied to the soil by pipetting 4 mL of treatment solution onto the soil in each pot. Galling was evaluated 3 weeks after inoculation as in Method 2.

Method 5. Soil and Foliar application to tomato plants

Steps from both Methods 2 and 4 were followed except that tomato plants were grown in 5.0×5.0 cm² pots and inoculation was made by pipetting approximately 7000 eggs in 4 mL onto the soil of each pot 20 days after planting. The day after inoculation, treatments were applied to the soil by pipetting 2 mL of treatment solution onto the soil of each pot and the leaves were sprayed with 1.5 mL of treatment solution. Galling was evaluated 3 weeks after inoculation as in Method 2.

TABLE A

| COMPD | RATE ppm | RATE mg/pot | METHOD 1* | METHOD 2** | METHOD 3** | METHOD 4** | METHOD 5** |
|---|---|---|---|---|---|---|---|
| 1 | 1000 | | 100 | 3 | | | |
|   | 500  | | 93  |   | | | |
|   | 250  | | 85  |   | | | |
|   |      | 1 |     |   | 3 | 3 | 3 |
| 2 | 1000 |   | 90  |   |   |   |   |
|   |      | 1 |     |   | 3 |   |   |
| 3 | 1000 |   | 65  |   |   |   |   |
|   | 500  |   | 51  |   |   |   |   |
|   |      | 1 |     |   | 3 |   |   |
| 4 | 1000 |   | 80  |   |   |   |   |
|   |      | 1 |     |   | 0 |   |   |
| 5 | 1000 |   | 84  |   |   |   |   |
|   |      | 1 |     |   | 3 |   |   |
| 6 | 1000 |   | 88  |   |   |   |   |
|   |      | 1 |     |   | 2 |   |   |
| 7 | 1000 |   | 89  | 1 |   |   |   |
|   |      | 1 |     |   |   | 3 |   |
| 8 | 1000 |   | 25  |   |   |   |   |
|   |      | 1 |     |   | 2 |   |   |
| 9 | 1000 |   | 100 | 3 |   |   |   |
|   | 500  |   | 85  |   |   |   |   |
|   | 250  |   | 70  |   |   |   |   |
|   |      | 1 |     |   | 2 | 3 |   |
| 10 | 1000 |  | 51  |   |   |   |   |
|   |      | 1 |     |   | 0 |   |   |
| 11 | 1500 |  |     | 1 |   |   |   |
|    | 1000 |  | 100 |   |   |   |   |
|    | 500  |  | 62  |   |   |   |   |
|    | 250  |  | 80  |   |   |   |   |
|    |      | 1 |    |   | 2 |   |   |
|    |      | 1.5 |  |   |   | 2 |   |
| 12 | 1000 |  | 76  | 2 |   |   |   |
|    |      | 1 |    |   |   | 2 |   |
| 13 | 1000 |  | 85  | 2 |   |   |   |
|    |      | 1 |    |   |   | 2 |   |
| 14 | 1000 |  | 32  |   |   |   |   |
|    |      | 1 |    |   | 1 |   |   |
| 15 | 1000 |  | 25  |   |   |   |   |
|    |      | 1 |    |   | 0 |   |   |
| 16 | 1000 |  | 75  |   |   |   |   |
|    |      | 1 |    |   | 0 |   |   |
| 17 | 1000 |  | 50  |   |   |   |   |
|    |      | 1 |    |   | 0 |   |   |
| 18 | 1000 |  | 38  |   |   |   |   |
|    |      | 1 |    |   | 0 |   |   |
| 19 | 1000 |  | 0   |   |   |   |   |
|    |      | 1 |    |   | 1 |   |   |
| 20 | 1000 |  | 51  | 0 |   |   |   |
|    |      | 1 |    |   |   | 3 |   |
| 21 | 1000 |  | 51  |   |   |   |   |
|    |      | 1 |    |   | 0 |   |   |
| 22 | 1000 |  | 98  | 2 |   |   |   |
|    |      | 1 |    |   | 2 | 0 | 2 |
| 23 | 1000 |  | 98  | 2 |   |   |   |
|    |      | 1 |    |   | 0 |   |   |
| 24 | 1000 |  | 73  | 2 |   |   |   |
|    |      | 1 |    |   | 0 | 3 |   |
| 25 | 1000 |  | 80  | 2 |   |   |   |
|    |      | 1 |    |   | 3 | 3 |   |
| 26 | 1000 |  | 79  |   |   |   |   |
|    |      | 1 |    |   | 0 |   |   |
| 27 | 1000 |  | 65  | 2 |   |   |   |
|    |      | 1 |    |   | 2 | 3 |   |
| 28 | 1000 |  | 78  |   |   |   |   |
|    |      | 1 |    |   | 0 |   |   |
| 29 | 1000 |  | 78  | 0 |   |   |   |
|    |      | 1 |    |   | 0 | 1 |   |
| 30 | 1000 |  | 78  | 1 |   |   |   |
|    |      | 1 |    |   | 0 |   |   |
| 31 | 1000 |  | 51  |   |   |   |   |
|    |      | 1 |    |   | 0 |   |   |

TABLE A-continued

| COMPD | RATE ppm | RATE mg/pot | METHOD 1* | METHOD 2** | METHOD 3** | METHOD 4** | METHOD 5** |
|---|---|---|---|---|---|---|---|
| 32 | 1000 | | 73 | 1 | | | |
| 33 | 1000 | 1 | 74 | | 0 | 0 | |
| 34 | 1000 | 1 | 72 | | 0 | | |
| 35 | 1000 | 1 | 98 | 3 | 0 | | |
| 36 | 1000 | 1 | 94 | 2 | 2 | 1 | 2 |
| 37 | 1000 | 1 | 86 | 3 | 2 | 3 | |
| 38 | 1000 | 1 | 91 | 3 | | 2 | |
| 39 | 1000 | 1 | 76 | 3 | | 2 | |
| 40 | 1000 | 1 | 90 | 3 | | 2 | |
| 41 | 1000 | 1 | 13 | 2 | 2 | 3 | |
| 42 | 1000 | 1 | 81 | 3 | | 3 | |
| 43 | 1000 | 1 | 0 | 0 | 2 | 3 | |
| 44 | 1000 | 1 | 100 | 1 | 2 | 2 | |
| 45 | 1000 | 0.2 | 94 | 2 | 2 | 0 | 2 |
|  | 500 | | 35 | | | | |
|  | 250 | | 14 | | | | |
| 46 | 1000 | 1 | 100 | 3 | 0 | 3 | |
|  | 500 | | 100 | | | | |
|  | 250 | | 92 | | | | |
| 47 | 1000 | 1 | 100 | 2 | 2 | | |
|  | 500 | | 94 | | | | |
|  | 250 | | 44 | | | | |
| 48 | 1000 | 1 | 100 | 3 | | 2 | |
| 49 | 1000 | 1 | | 3 | | 3 | |
| 50 | 1000 | 1 | 0 | | 0 | 1 | |
| 51 | 1000 | 1 | | 0 | 2 | | |
| 52 | 1000 | 1 | | 0 | 2 | 3 | |
| 53 | 1000 | 1 | | 0 | 2 | 2 | |
| 54 | 1000 | 1 | 0 | 0 | 0 | 1 | |
| 55 | 1000 | 1 | 91 | 0 | 2 | 2 | |
| 56 | 1000 | 1 | 92 | 3 | | 1 | |
| 57 | 1000 | 1 | 94 | 2 | | 1 | |
| 58 | 1000 | 1 | 94 | 2 | 2 | 3 | |
| 59 | 1000 | 1 | | 0 | | 3 | |
| 60 | 1000 | 1 | 78 | 2 | | 1 | |
| 61 | 1000 | 1 | | 2 | | 2 | |
| 62 | 1000 | 1 | 100 | 3 | | 3 | |
| 63 | 1000 | 1 | 92 | 3 | | 3 | |
| 64 | 1000 | 1 | 96 | 1 | | 3 | |
| 65 | 1000 | 1 | 92 | 1 | | 1 | |
| 66 | 1000 | 1 | 100 | 0 | | 3 | |
| 67 | 1000 | 1 | 92 | 1 | 0 | 0 | |
| 69 | 1000 | 1 | 96 | 1 | 1 | 2 | |
| 70 | 1000 | 1 | 51 | 3 | | 3 | |
| 71 | 1000 | 1 | 25 | 0 | | 3 | |
| 72 | 1000 | 1 | | | 0 | 1 | |
| 73 | 1000 | 1 | | | 2 | 2 | |
| 74 | 1000 | 1 | | | 0 | 2 | |
| 75 | 1000 | 1 | 0 | 1 | 2 | | |
| 76 | 1000 | 1 | 91 | 2 | 0 | 3 | |
| 77 | 1000 | 1 | | | 0 | 3 | |
| 78 | 1000 | 1 | | | 0 | 1 | |
| 79 | 1000 | 1 | 0 | 1 | | 2 | |
| 80 | 1000 | | 100 | | 2 | 3 | |
|  | 500 | | 94 | | | | |
|  | 250 | | 0 | | | | |
| 81 | 1000 | 1 | 92 | | | 1 | |
|  | 500 | | 84 | | | | |
|  | 250 | | 62 | | | | |
| 82 | 1000 | 1 | 92 | | | 1 | |
|  | 250 | | 32 | | | | |
| 83 | 1000 | 1 | 100 | | | 1 | |
|  | 250 | | 78 | | | | |
| 84 | 1000 | 1 | 12 | | | 1 | 1 |
| 85 | 1000 | 1 | 25 | | | 1 | 0 |
| 86 | 1000 | 1 | 0 | | | 1 | 0 |
| 87 | 1000 | 1 | 0 | | | 1 | 0 |
| 88 | 1000 | | 58 | | | 1 | 0 |
|  | 500 | | 30 | | | | |
|  | 250 | | 0 | | | | |
| 89 | 1000 | 1 | 25 | | | 1 | 3 |
| 90 | 1000 | 1 | 16 | | | | 0 |
| 91 | 1000 | | 100 | | | 2 | 3 |
|  | 500 | | 78 | | | | |
|  | 250 | | 13 | | | | |
| 92 | 1000 | 1 | 26 | | | 2 | 3 |
| 93 | 1000 | 1 | 94 | | | 0 | 1 |
| 94 | 1000 | 1 | 98 | | | 1 | 0 |
| 95 | 1000 | | 100 | | | 0 | 0 |
|  | 500 | | 76 | | | | |
|  | 250 | | 25 | | | | |
| 96 | 1000 | 1 | 0 | | | 3 | 0 |
| 97 | 1000 | 1 | 0 | | | 2 | 2 |
| 98 | 1000 | 1 | 0 | | | 1 | 1 |
|  | | 1 | | | | 2 | 3 |

TABLE A-continued

| COMPD | RATE ppm | mg/pot | METHOD 1* | 2** | 3** | 4** | 5** |
|---|---|---|---|---|---|---|---|
| 99 | 1000 | | 13 | | | | |
| | | 1 | | | | 2 | |
| 100 | 1000 | | 0 | | | | |
| | | 1 | | | | 2 | |
| 101 | 1000 | | 94 | | | | |
| | 500 | | 21 | | | | |
| | 250 | | 21 | | | | |
| | | 1 | | | | 2 | |
| 102 | 1000 | | 0 | | | | |
| | | 1 | | | 1 | 0 | |
| 103 | 1000 | | 0 | | | | |
| | | 1 | | | 1 | 0 | |
| 104 | 1000 | | 19 | | | | |
| | | 1 | | | 1 | 1 | |
| 105 | 1000 | | 90 | | | | |
| | | 1 | | | 3 | | |
| 106 | 1000 | | 90 | | | | |
| | | 1 | | | 3 | | |
| 107 | 1000 | | 88 | | | | |
| | | 1 | | | 3 | 3 | |
| 108 | 1000 | | 92 | | | | |
| | | 1 | | | 3 | 3 | |
| 109 | 1000 | | 76 | | | | |
| | | 1 | | | 1 | | |
| 110 | 1000 | | 92 | | | | |
| | | 1 | | | 3 | | |
| 111 | 1000 | | 78 | | | | |
| | | 1 | | | 1 | 3 | |
| 112 | 1000 | | 62 | | | | |
| | | 1 | | | 1 | 2 | |
| 113 | 1000 | | 51 | | | | |
| | | 1 | | | 3 | 2 | |
| 114 | 1000 | | 51 | | | | |
| | | 1 | | | 3 | 3 | |
| 115 | 1000 | | 97 | | | | |
| | 500 | | 85 | | | | |
| | 250 | | 70 | | | | |
| | | 1 | | | 3 | 3 | |
| 116 | 1000 | | 52 | | | | |
| | 500 | | 30 | | | | |
| | 250 | | 0 | | | | |
| | | 1 | | | 3 | 3 | |
| 117 | 1000 | | 94 | | | | |
| | 500 | | 76 | | | | |
| | 250 | | 67 | | | | |
| | | 1 | | | 2 | 3 | |
| 118 | 1000 | | 25 | | | | |
| | | 1 | | | 2 | 3 | |
| 119 | 1000 | | 36 | | | | |
| | 500 | | 36 | | | | |
| | 250 | | 0 | | | | |
| | | 1 | | | 3 | 3 | |
| 120 | 1000 | | 92 | | | | |
| | | 1 | | | 3 | 3 | |
| 121 | 1000 | | 36 | | | | |
| | 500 | | 36 | | | | |
| | 250 | | 42 | | | | |
| | | 1 | | | 3 | 3 | |
| 122 | 1000 | | 92 | | | | |
| | | 1 | | | 2 | 3 | |
| 123 | 1000 | | 94 | | | | |
| | 500 | | 92 | | | | |
| | 250 | | 51 | | | | |
| | | 1 | | | 3 | 3 | |
| 124 | 1000 | | 98 | | | | |
| | 500 | | 92 | | | | |
| | 250 | | 39 | | | | |
| | | 1 | | | 3 | 3 | |
| 125 | 1000 | | 61 | | | | |
| | | 1 | | | 3 | 2 | |
| 126 | 1000 | | 84 | | | | |
| | 500 | | 63 | | | | |
| | 250 | | 13 | | | | |
| | | 1 | | | 2 | 2 | |
| 127 | 1000 | | 13 | | | | |
| | 500 | | 0 | | | | |
| | | 1 | | | 2 | | |
| 128 | 1000 | | 0 | | | | |
| | | 1 | | | 3 | 3 | |
| 129 | 1000 | | 84 | | | | |
| | 500 | | 57 | | | | |
| | 250 | | 25 | | | | |
| | | 1 | | | 3 | 3 | |
| 130 | 1000 | | 92 | | | | |
| | 500 | | 63 | | | | |
| | 250 | | 0 | | | | |
| | | 1 | | | 3 | 2 | |
| 131 | 1000 | | 80 | | | | |
| | 500 | | 78 | | | | |
| | 250 | | 19 | | | | |
| | | 1 | | | 3 | 3 | |
| 132 | 1000 | | 84 | | | | |
| | 500 | | 41 | | | | |
| | 250 | | 0 | | | | |
| | | 1 | | | 2 | 1 | |
| 133 | 1000 | | 0 | | | | |
| | | 1 | | | 2 | 1 | |
| 134 | 1000 | | 57 | | | | |
| | 500 | | 13 | | | | |
| | 250 | | 13 | | | | |
| | | 1 | | | 3 | 3 | |
| 135 | 1000 | | 0 | | | | |
| | | 1 | | | 2 | 0 | |
| 136 | 1000 | | 80 | | | | |
| | 500 | | 13 | | | | |
| | 250 | | 38 | | | | |
| | | 1 | | | 3 | 2 | |
| 137 | 1000 | | 71 | | | | |
| | | 1 | | | 2 | 2 | |
| 147 | 1000 | | 96 | | | | |
| | 500 | | 76 | | | | |
| | 250 | | 44 | | | | |
| | | 1 | | | 2 | | |
| 148 | 1000 | | 0 | | | | |
| | | 1 | | | 3 | | |
| 149 | 1000 | | 0 | | | | |
| | | 1 | | | 1 | | |
| 150 | 1000 | | 0 | | | | |
| | 500 | | 15 | | | | |
| | 250 | | 15 | | | | |
| | | 1 | | | 0 | | |

*Percent Control of Disease
**Disease Control Rating:
0 = No disease control
1 = 50–74% disease, control
2 = 75–90% disease control
3 = 91–100% disease control B. Soybean cyst nematode test Compound 1 was tested for effectiveness in controlling the soybean cyst nematode (*Heterodera glycines*) by foliar application. A sandy soil was infested with approximately 100 soybean cyst nematode eggs per cc of soil. Approximately 350 cc of the infested soil was placed into each 4-inch square pot. Three soybean seeds, Glycine max variety Williams-82, were placed on top of the infested soil and covered with a layer of uninfected sandy soil.

Foliar applications were begun when the plant reached the unifoliate leaf stage. Applications were made as a single unifoliate spray or in sequential sprays at unifoliate plus seven days or unifoliate plus seven and plus fourteen days. The test compound was dissolved in water with 1% glycerin and 0.1% Tween®20. At each spraying, the soil surface was covered to prevent soil contact. The applications, using the rates listed below, were made to the point of runoff.

Final disease evaluations were made approximately five weeks after planting by counting the number of cysts on each root system. Control was determined by percent reduction in average number of cysts per root on treated plants as compared to the inoculated, water/glycerin/Tween®20 formulation control.

TABLE B

| Rate (ppm) | Timing | Percent Control |
|---|---|---|
| 1000 | unifoliate | 70 |
| 2000 | unifoliate | 62 |
| 1000 | unifoliate + 7 d | 100 |
| 2000 | unifoliate + 7 d | 94 |
| 1000 | unifoliate + 7 d + 14 d | 100 |
| 2000 | unifoliate + 7 d + 14 d | 100 |

C. Insect and acarid tests

Compounds of the present invention were tested for effectiveness in controlling the two spotted spider mite, *Tetranychus urticae* or TSSM; the green peach aphid, *Myzus persicae* or GPA; and the southern corn rootworm, *Diabrotica undecimpunctata* or CRW, by foliar application.

In initial tests to determine activity against aphids, three week old chinese cabbage (*Brassica chinensis*) were infested with green peach aphid adults from leaf pieces of culture plants. Newly infested plants were left in growth chambers until insect populations increased to greater than forty insects per leaf. The most uniformly infested plants were selected for testing purposes. Appropriate amounts of test materials were dissolved directly in a water formulation with 1% glycerin and 0.1% Tween®20. Plants were sprayed to runoff on both upper and lower leaf surfaces. Five plants for each test solution were sprayed. The sprayed plants were transferred to a hood where they were kept until the spray had dried. Plants were transferred back to growth chamber for five days before making final percent control ratings.

For two spotted spider mite tests, soybeans (*Glycine max*) grown to the unifoliate stage, or cotton (*Gossypium hirsutum*) grown to the full cotyledon stage were utilized. Leaf discs made using a #6 cork borer were removed from culture plants infested with adult mites and eggs and placed on the upper unifoliate leaf surface of the soybean plants or cotyledons of the cotton plants. After the mites had migrated and infested the entire plant (6–10 days), the leaf discs were removed. The most uniformly infested plants were selected for testing purposes and sprayed with test solutions as described above using five plants per treatment. Five days after application all leaves were examined and adult mites on the underside of leaves were counted. Control was calculated by percent reduction in average number of mites on treatment plants as compared to the inoculated water/formulation control.

Tests against southern corn rootworm were conducted using four corn (*Zea mays*) seeds planted in each of three inch pots and grown in the greenhouse until approximately six inches tall. Small holes were scratched into the soil surface near the roots of each plant and ten first instar larvae of southern corn rootworm were placed in the holes. One day after infestation, leaves of the corn plants were sprayed to runoff with test solutions of the same formulation as above. Seven days after spraying, larvae were recovered from soil by soaking pots in 10M MgSO$_4$ solution. The number of living larvae were averaged for each treatment and the percent control calculated.

TABLE C

| Compound | Rate (ppm) | Percent Control | | |
|---|---|---|---|---|
| | | GPA | TSSM | CRW |
| 1 | 2000 | 60 | 85 | |
| | 1000 | | | 35 |
| | 500 | 25 | 84 | |
| 11 | 2000 | 20 | 28 | |
| | 1000 | | | 87 |
| | 500 | 0 | | |
| 22 | 1000 | 0 | 80 | 58 |
| 23 | 1000 | 30 | 6 | 75 |
| 26 | 1000 | 40 | 49 | 80 |
| 35 | 1000 | 60 | | 87 |
| 37 | 1000 | 30 | | 80 |
| 38 | 1000 | 70 | 84 | 80 |
| 46 | 1000 | 100 | 100 | 80 |
| | 500 | 90 | | |
| | 200 | | 80 | |
| | 100 | 70 | | |
| | 40 | | 60 | |

D. Potato seed treatments

Compound 1 of the present invention was tested for effectiveness in controlling root knot nematode (*Meloidogyne incognita*) by application to potato seed pieces. The compound was also tested by foliar application as a comparison.

Potato tubers were cut so as to retain at least two eyes per piece. For each treatment level the tuber pieces were weighed and placed in a mixture of the compound and enough powdered clay to expose the pieces to the specified treatment rate at a constant treatment volume. The pieces were agitated until the surfaces were coated and planted, one piece per one-gallon pot. Each pot was inoculated with 50,000 eggs.

In the foliar application, the plants were each sprayed with a solution of Compound 1 in water with 1% glycerin and 0.05% Tween®20. The spray was applied so as to evenly distribute the compound over the surfaces of all leaves. Each plant was sprayed four times, two weeks apart, and was inoculated as for the tuber pieces either at planting or at three days prior to each treatment. The results are shown in Table D.

TABLE D

| RATE | | INOCULATION | PERCENT DISEASE |
|---|---|---|---|
| mg/kg seed | ppm fol.spr. | TIME | CONTROL |
| 500 | | PLANTING | 99 |
| 250 | | | 97 |
| 125 | | | 77 |
| | 2000 | PLANTING | 84 |
| | 1000 | | 69 |
| | 500 | | 46 |
| | 2000 | PRIOR TO SPRAYING | 100 |
| | 1000 | | 97 |
| | 500 | | 92 |
| 0 | 0 | PLANTING | 0 |

What is claimed is:
1. 3,4,4-trifluoro-3-butene-1-tosylate.
2. 3,4,4-trifluoro-3-butene-1-mesylate.

* * * * *